United States Patent
Narine et al.

(10) Patent No.: US 8,741,822 B2
(45) Date of Patent: Jun. 3, 2014

(54) ESTERS FOR USE AS A BASE STOCK AND IN LUBRICANT APPLICATIONS

(75) Inventors: Suresh Narine, Peterborough (CA); Shaojun Li, Peterborough (CA); Ali Mahdevari, Peterborough (CA); Laziz Bouzidi, Peterborough (CA); Stephen Augustine DiBiase, Willowbrook, IL (US); Syed Q. A. Rizvi, Painesville, OH (US)

(73) Assignee: Trent University, Peterborough, Ontario (CA)

( * ) Notice: Subject to any disclaimer, the term of this patent is extended or adjusted under 35 U.S.C. 154(b) by 0 days.

(21) Appl. No.: 13/026,268

(22) Filed: Feb. 13, 2011

(65) Prior Publication Data

US 2012/0208732 A1 Aug. 16, 2012

(51) Int. Cl.
*C10M 105/40* (2006.01)
*C10M 105/42* (2006.01)

(52) U.S. Cl.
CPC .......... *C10M 105/40* (2013.01); *C10M 105/42* (2013.01); *C10M 2207/28* (2013.01); *C10M 2207/2805* (2013.01); *C10M 2207/30* (2013.01); *C10M 2207/301* (2013.01); *C10N 2240/105* (2013.01); *C10N 2240/40* (2013.01); *C10N 2250/10* (2013.01)
USPC ........................... 508/465; 508/463; 508/506

(58) Field of Classification Search
CPC ............. C10M 105/40; C10M 105/42; C10M 2207/28; C10M 2207/2805; C10M 2207/30; C10M 2207/301; C10N 2240/08; C10N 2240/105; C10N 2210/40; C10N 2250/10
USPC .......................................... 508/463, 465, 506
See application file for complete search history.

(56) References Cited

U.S. PATENT DOCUMENTS

| | | | |
|---|---|---|---|
| 2,886,590 A | 5/1959 | Montgomery et al. |
| 3,048,623 A | 8/1962 | Matuszak et al. |
| 4,138,347 A | 2/1979 | Crawford |
| 4,510,093 A | 4/1985 | Hülsmann |
| 6,018,063 A | 1/2000 | Isbell et al. |
| 6,316,649 B1 | 11/2001 | Cermak et al. |
| 7,871,967 B2 | 1/2011 | Miller et al. |
| 8,304,574 B2 | 11/2012 | Elomari et al. |
| 8,410,033 B2 | 4/2013 | Zhou et al. |
| 2009/0198075 A1 | 8/2009 | Miller et al. |
| 2010/0120642 A1 | 5/2010 | Miller et al. |
| 2012/0129746 A1 | 5/2012 | Benecke et al. |

FOREIGN PATENT DOCUMENTS

EP 0 069 946 A1 1/1983
WO WO 2009/020667 A1 2/2009

OTHER PUBLICATIONS

Swern et al., Aliphatic esters of the 9,10-dihydroxystearic acids, 1945, Journal of American Chemical Society, 67, 902-3, ISSN: 002-7863.*

(Continued)

*Primary Examiner* — Taiwo Oladapo
(74) *Attorney, Agent, or Firm* — Nirav Patel

(57) ABSTRACT

This invention relates to base ester compounds and complex ester compounds that can be used as a base stock for lubricant applications or a base stock blend component for use in a finished lubricant or for particular applications, and methods of making the same. The base ester compounds and complex esters described herein comprise dimer and/or trimer esters, and their respective branched derivatives.

12 Claims, 19 Drawing Sheets

Procedure 1)

Procedure 2)

Synthesis of Dimer Esters

(56) References Cited

OTHER PUBLICATIONS

Bouzidi, Laziz et al., "Lubricating and waxy esters I: Synthesis, crystallization, and melt behavior of linear monoesters," Chemistry and Physics of Lipids, vol. 165, 2012, pp. 38-50.

Doll, Kenneth M. et al., "Synthesis of Branched Methyl Hydroxy Stearates Including an Ester from Bio-Based Levulinic Acid," Ind. Eng. Chem. Res., vol. 46, 2007, pp. 3513-3519.

Garcia-Zapateiro, L.A. et al., "Oleins as a source of estolides for biolubricant applications," Grasas y Aceites, vol. 61, No. 2, 2010, pp. 171-174.

Moser, Bryan R. et al., "Diesters from Oleic Acid: Synthesis, Low Temperature Properties, and Oxidation Stability," J. Amer. Oil Chem. Soc., vol. 84, 2007, pp. 675-680.

Salimon, Jumat, "Oleic Acid Diesters: Synthesis, Characterization and Low Temperature Properties," European Journal of Scientific Research, vol. 32, No. 2, 2009, pp. 216-222.

Yao, Linxing et al., "Melting Points and Viscosities of Fatty Acid Esters that are Potential Targets for Engineered Oilseed," J. Am. Oil Chem. Soc., vol. 85, 2008, pp. 77-82.

Yao, Linxing et al., "Synthesis and Physical Properties of Potential Biolubricants based on Ricinoleic Acid," J. Am. Oil Chem. Soc., vol. 87, 2010, pp. 937-945.

International Search Report for International Application No. PCT/US2012/024876, dated May 25, 2012, 3 pages.

International Preliminary Report on Patentability for International Application No. PCT/US2012/024876, dated Aug. 13, 2013, 7 pages.

* cited by examiner

Procedure 1)
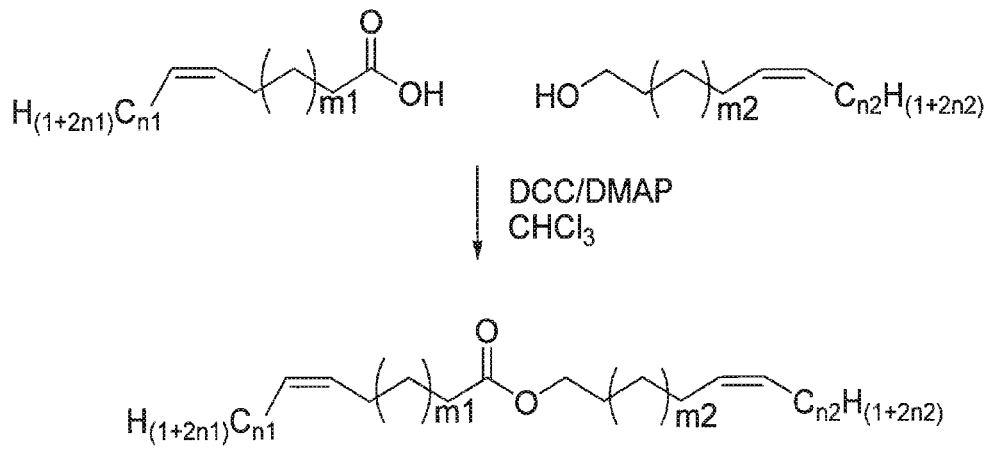
Procedure 2)
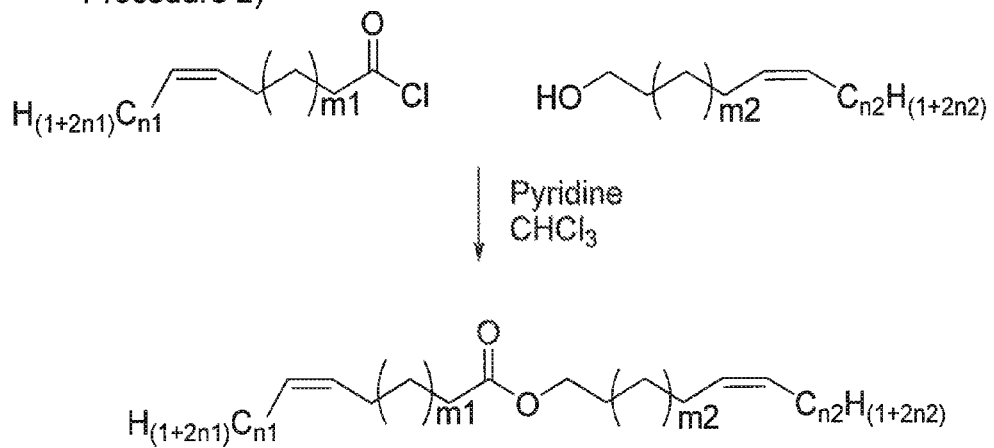
Figure 1: Synthesis of Dimer Esters

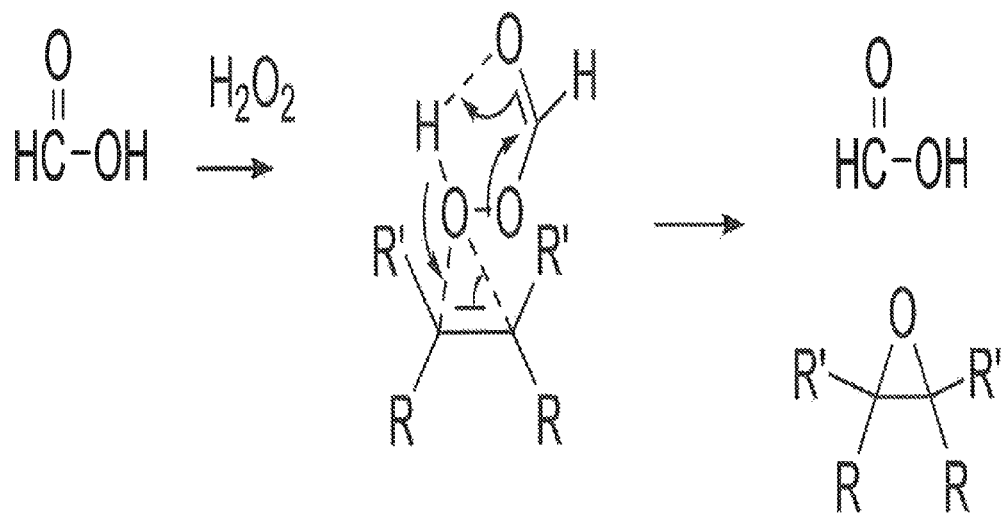
Figure 2: Epoxidation of alkene
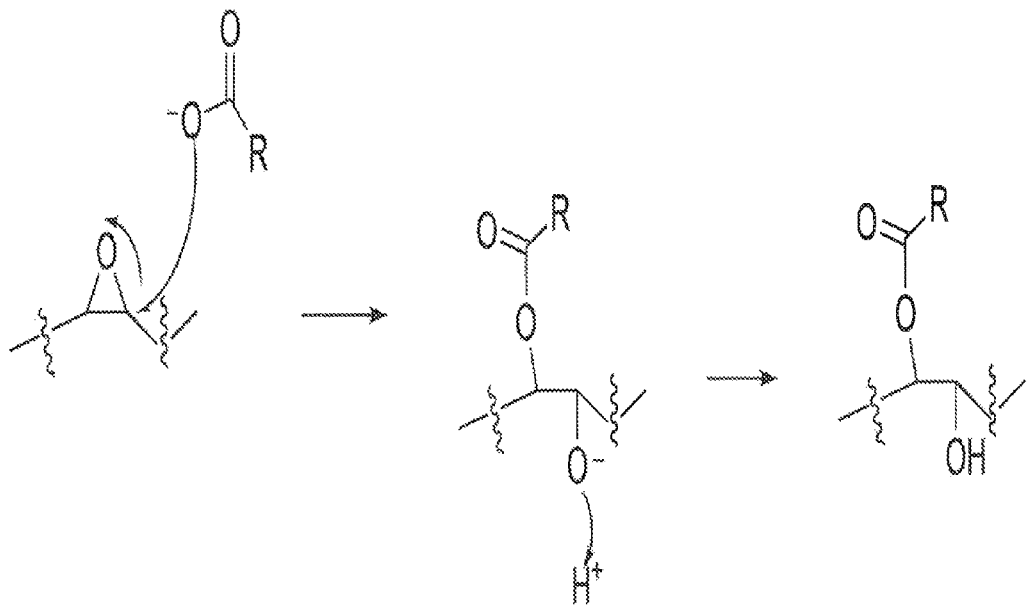
Figure 3: Ring opening esterification of epoxides

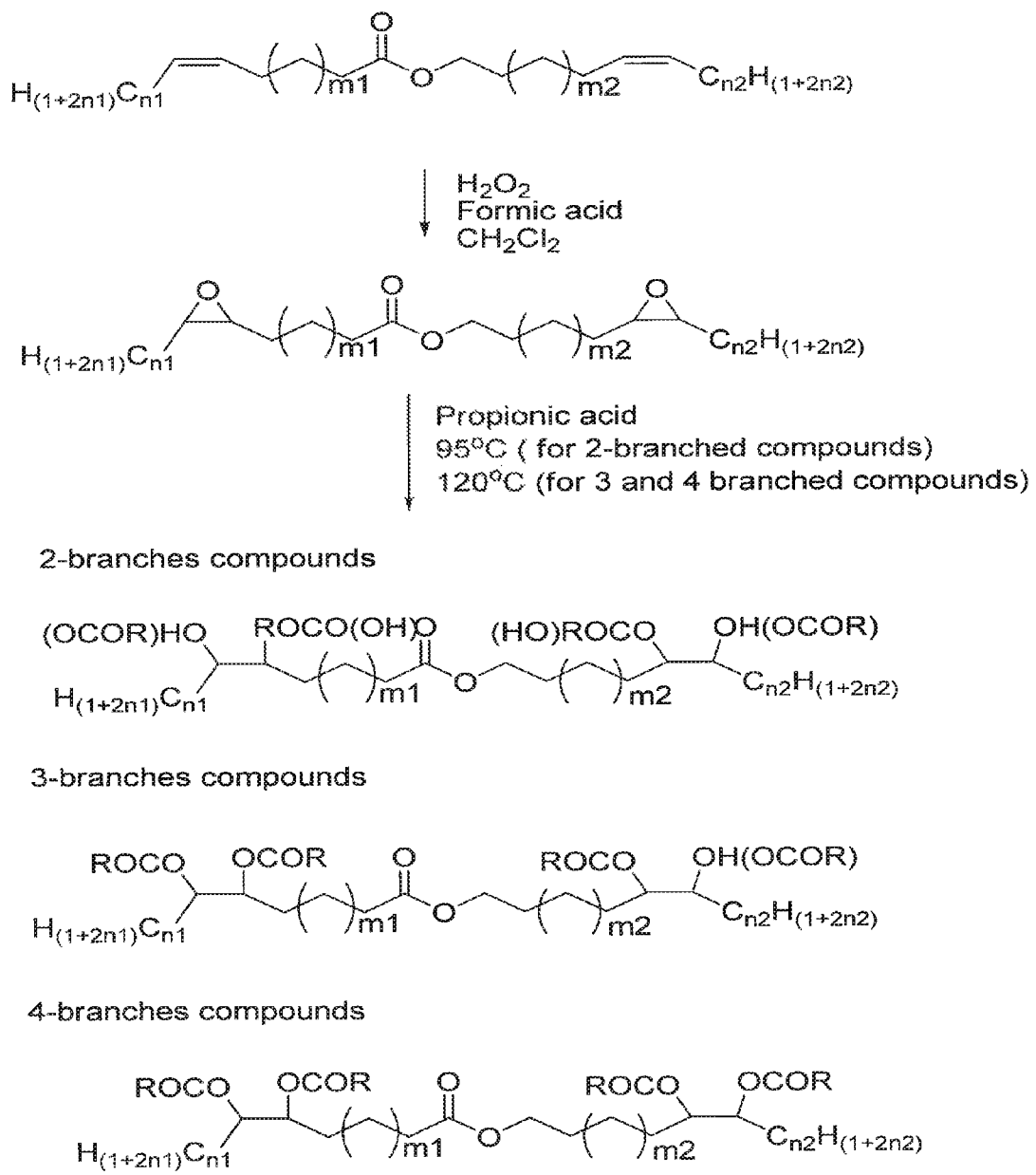
Figure 4: Syntheses of dimer ester branched compounds

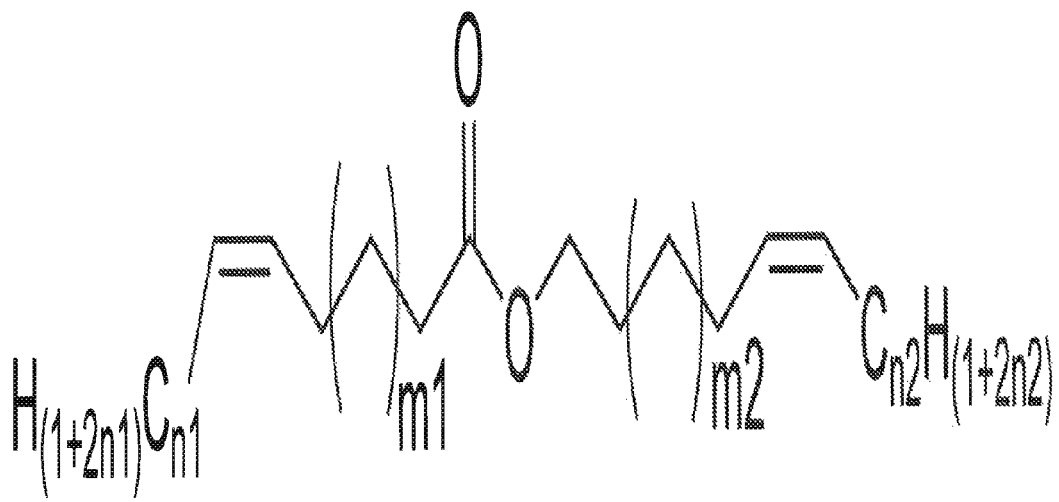
Figure 4A: Generalized structure for base dimer ester
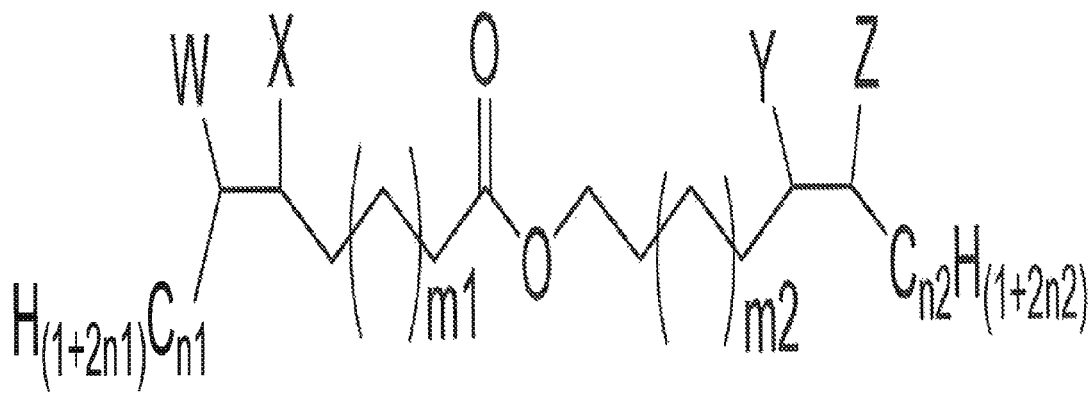
Figure 4B: Generalized structure for dimer ester branched derivatives nonbranch
3-branched
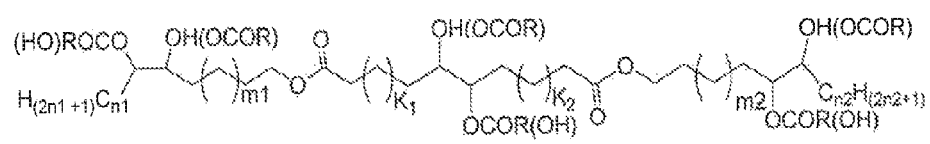
4-branched
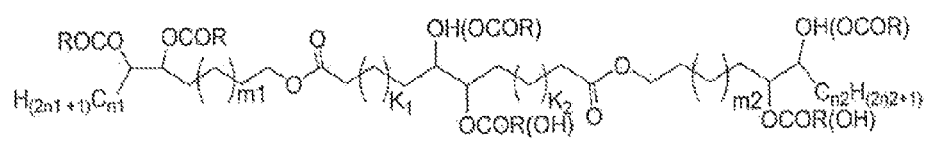
5-branched
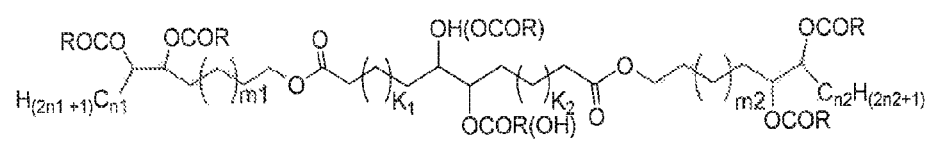
6-branched
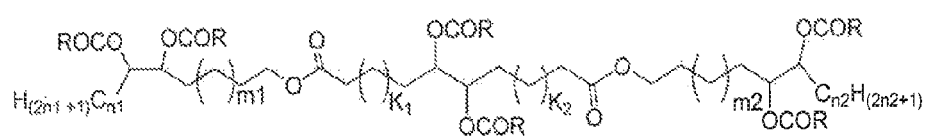
Figure 5: Trimer esters and their branched compounds

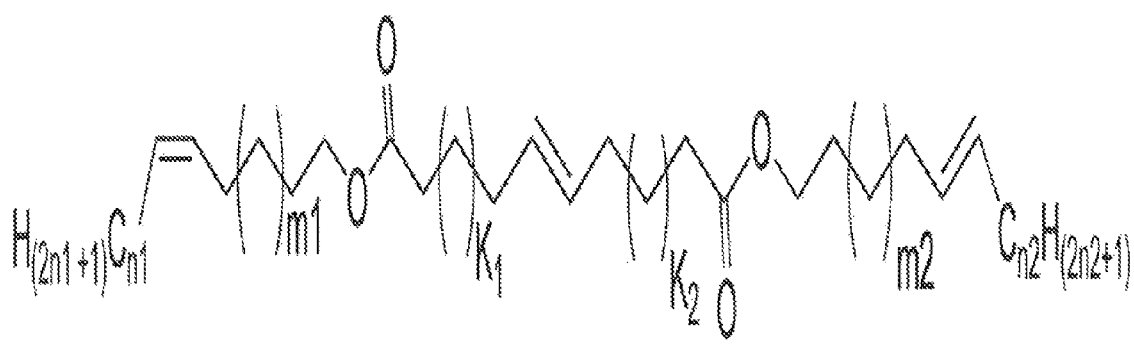
Figure 5A: Generalized structure for base trimer esters
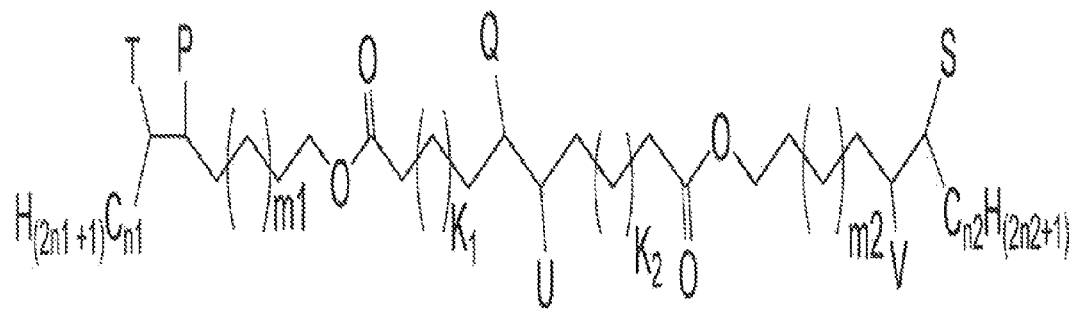
Figure 5B: Generalized compound for trimer ester branched derivatives

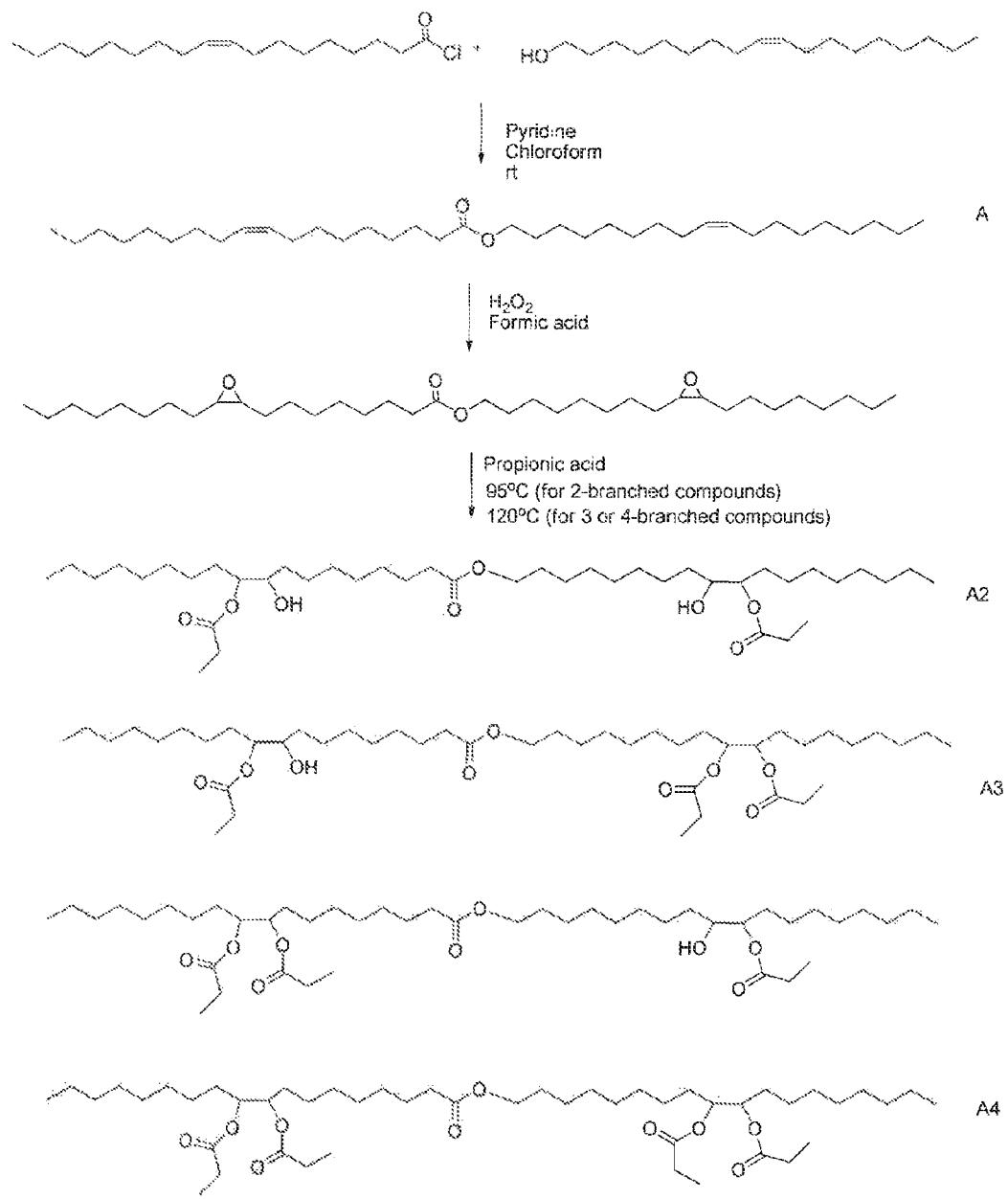
Figure 6: Synthesis of Compound A and its branched derivatives

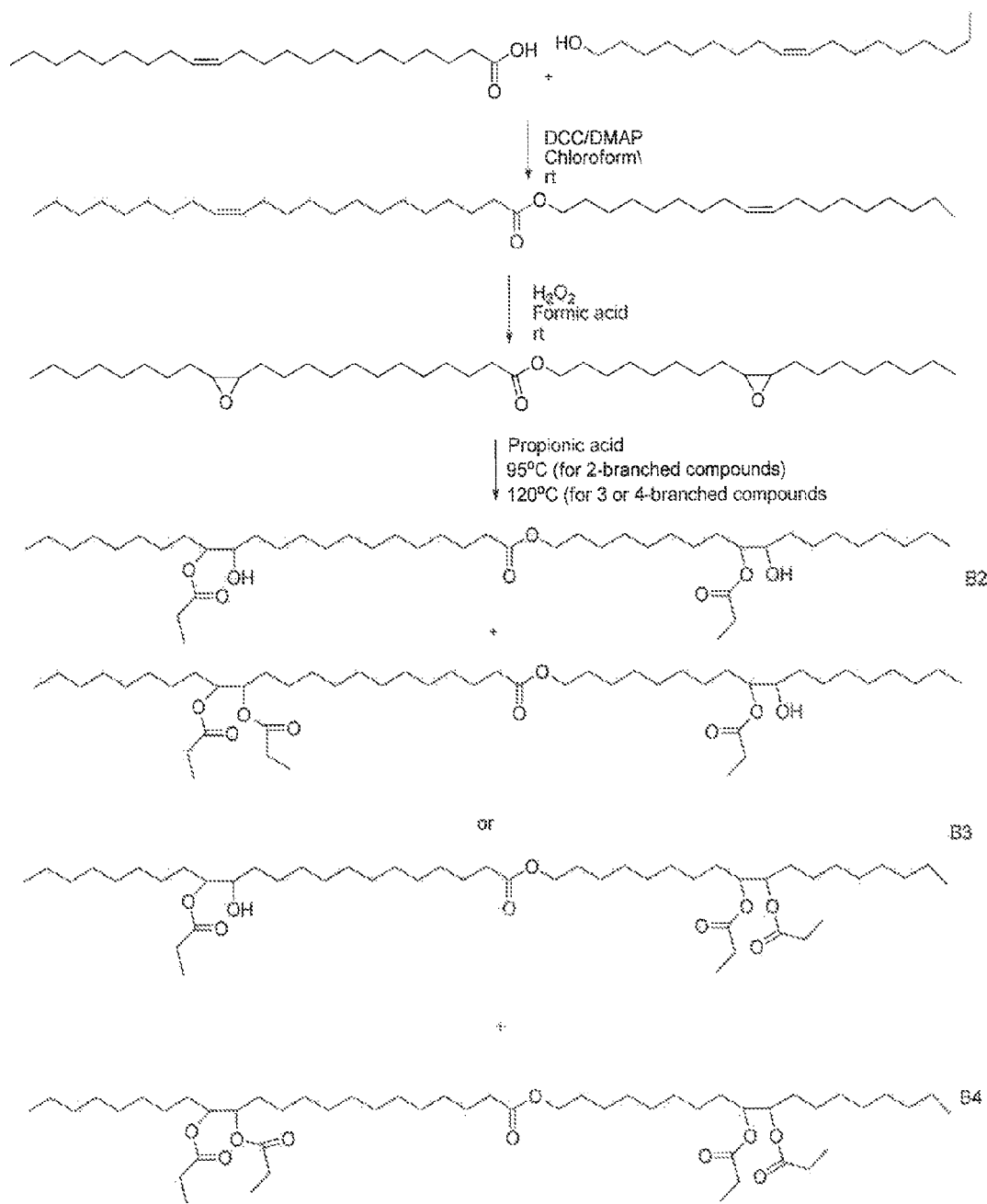
Figure 7: Synthesis of Compound B and its branched derivatives

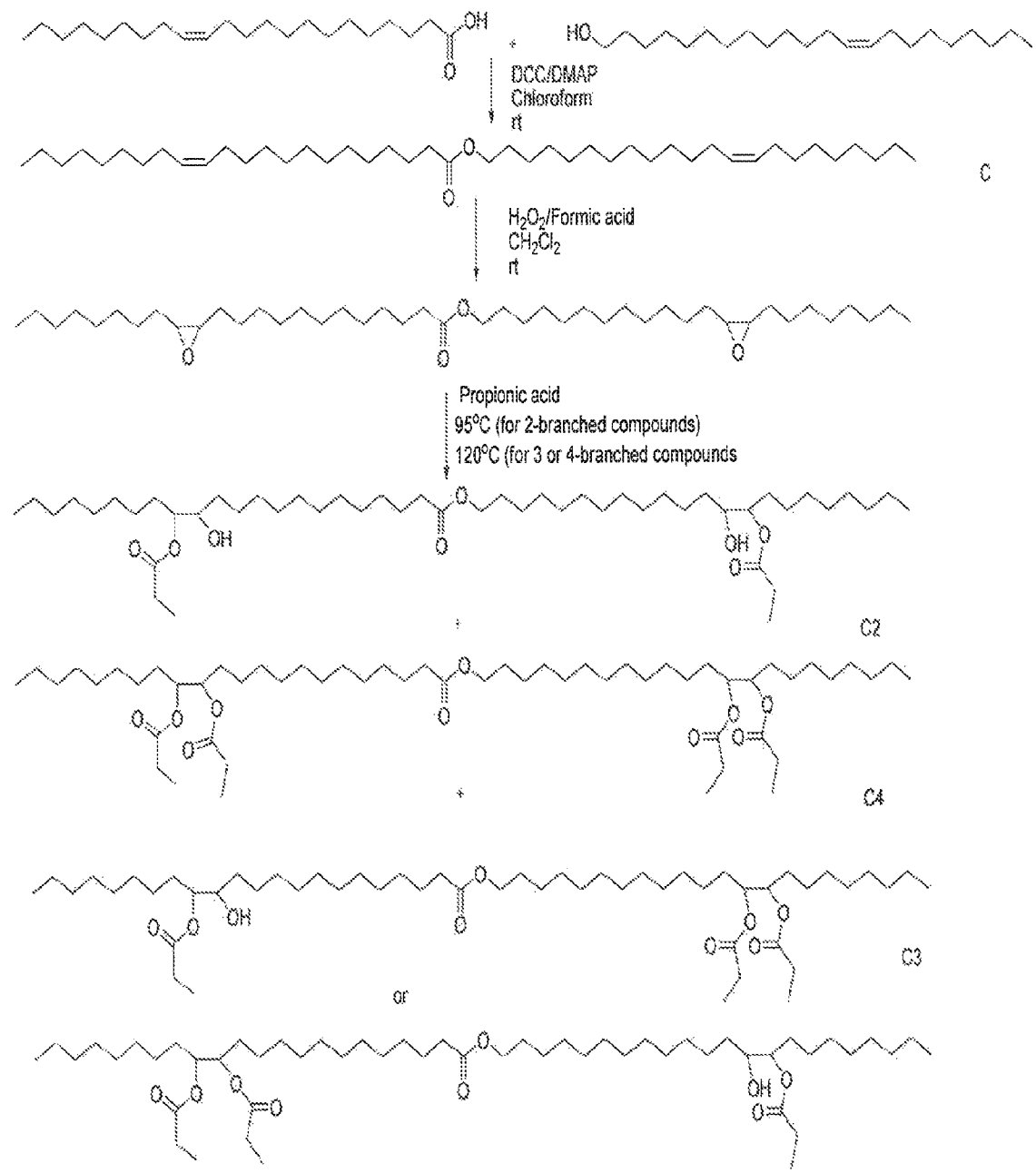
Figure 8: Synthesis of Compound C and its branched derivatives

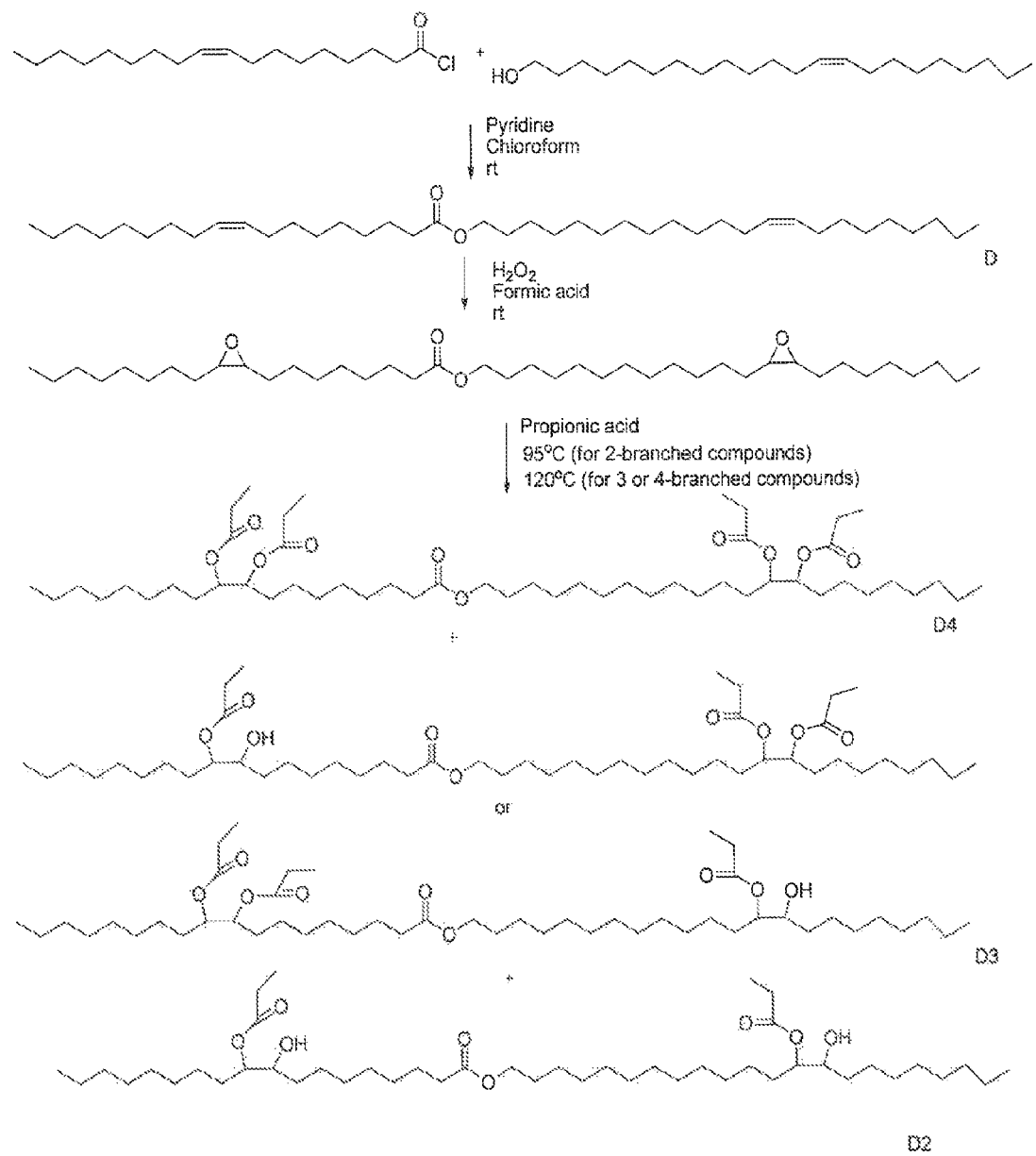
Figure 9: Synthesis of Compound D and its branched derivatives

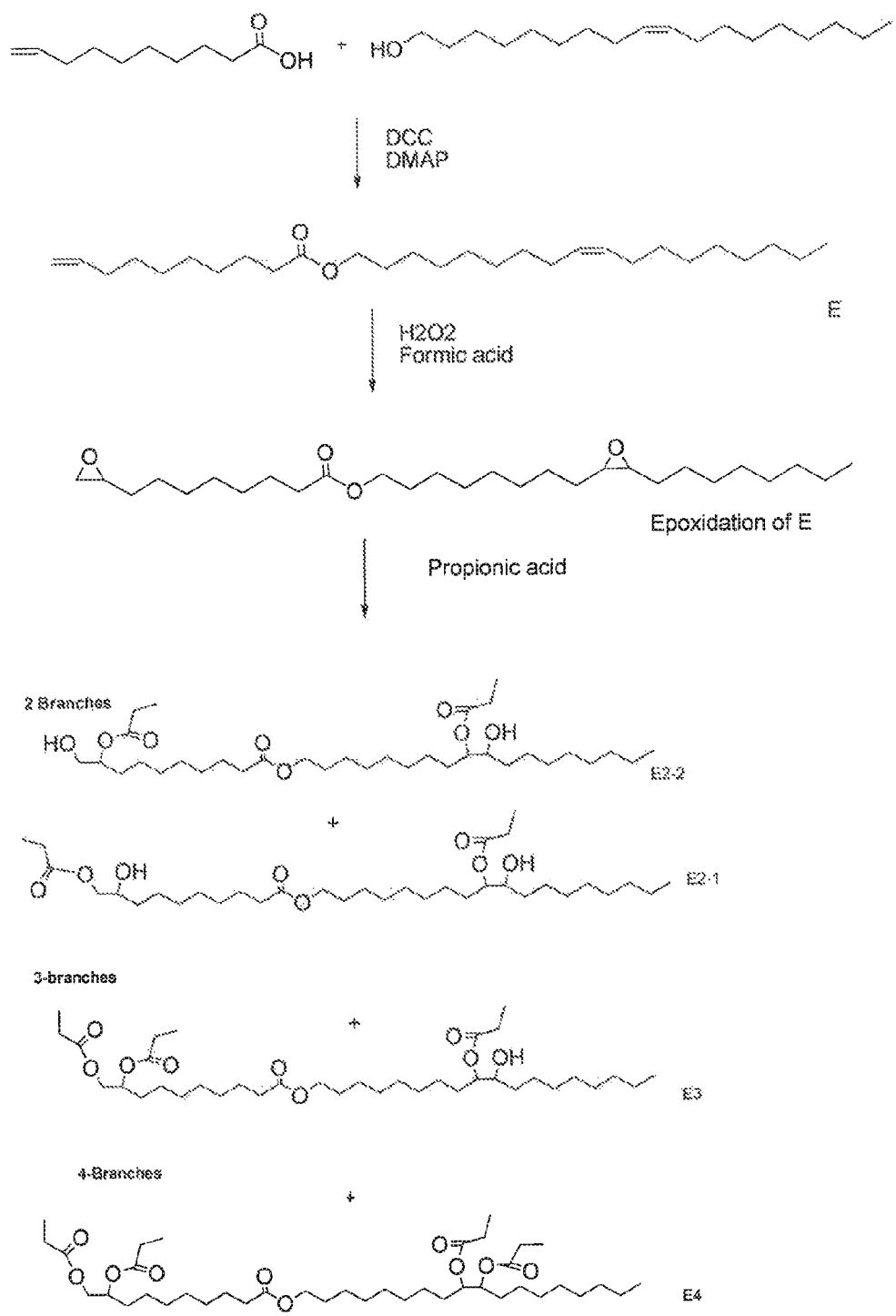
Figure 10: Synthesis of Compound E and its branched derivatives

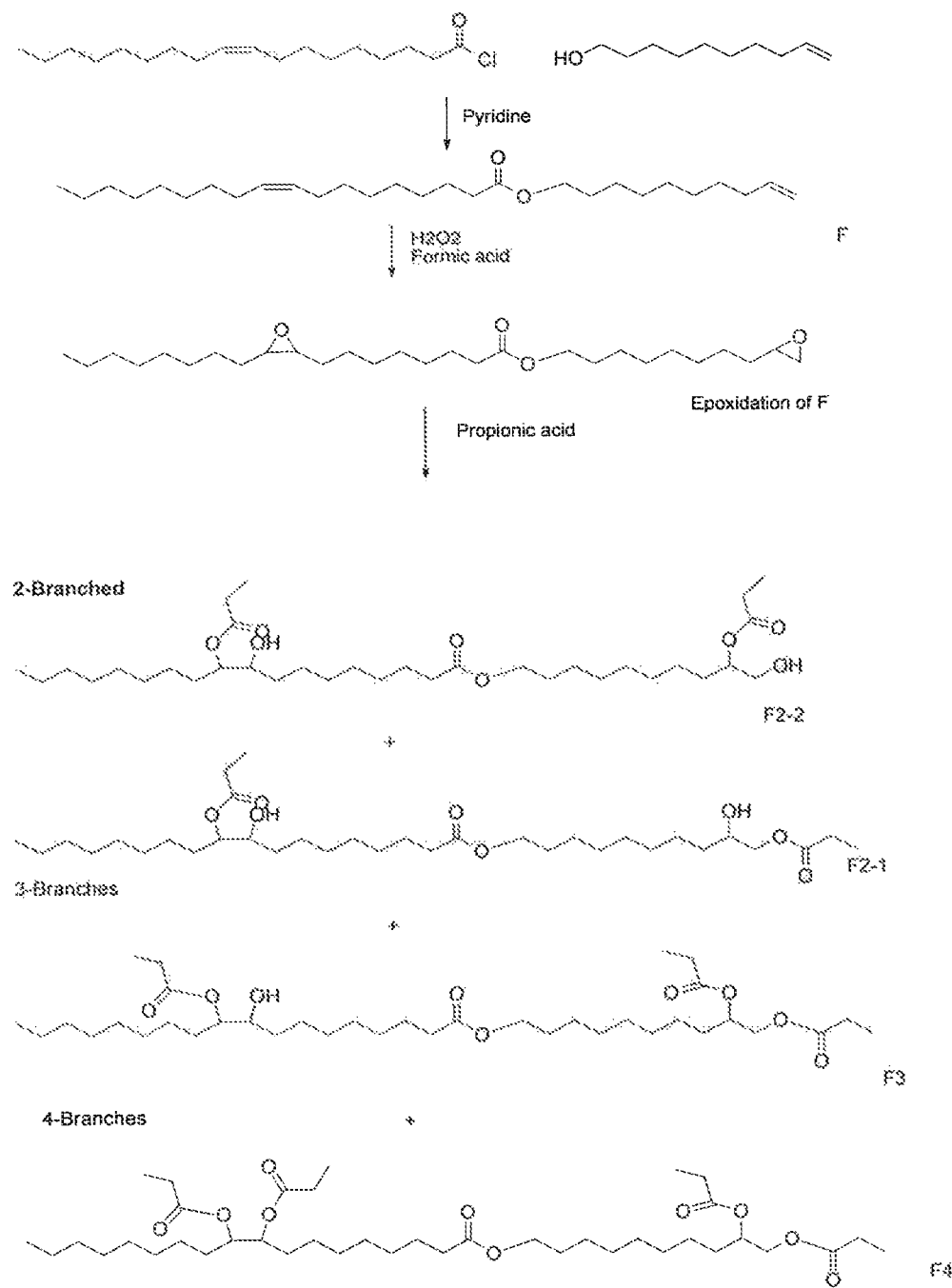
Figure 11: Synthesis of Compound F and its branched derivatives

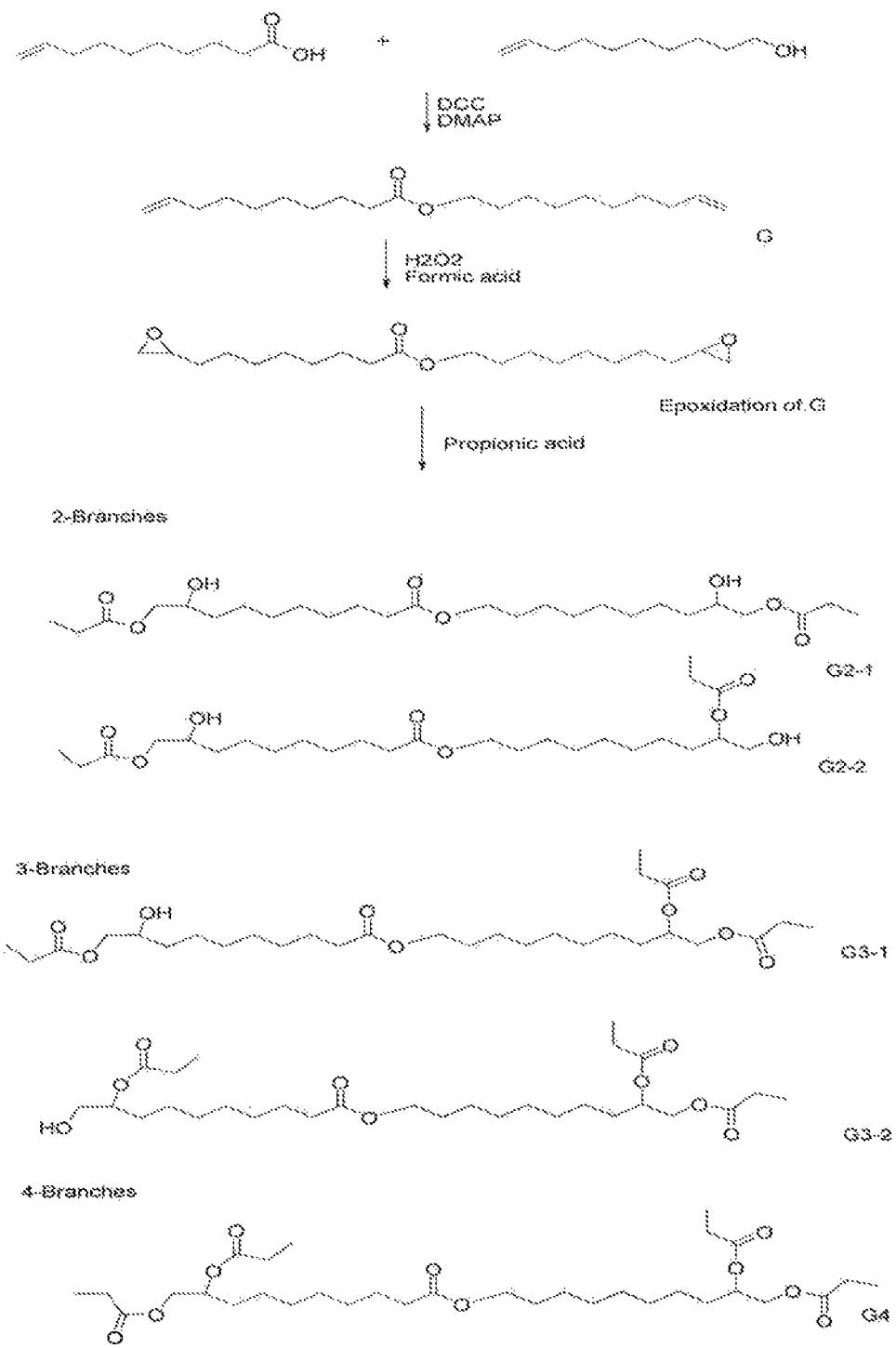
Figure 12: Synthesis of Compound G and its branched derivatives

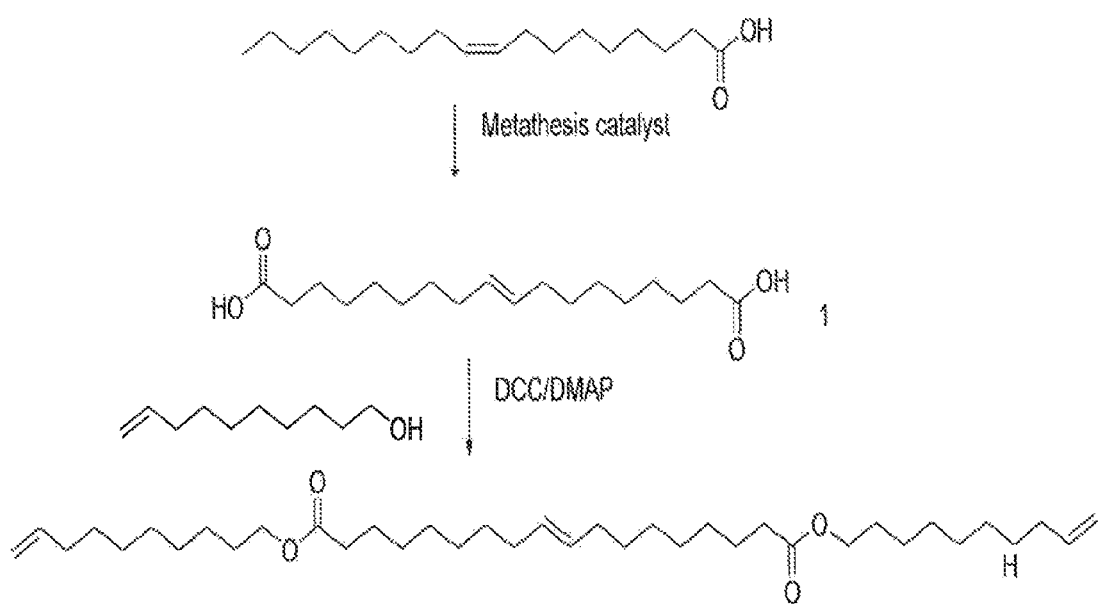
Figure 13: Synthesis of (E)-didec-9-enyl octadec-9-enedioate (Compound H)

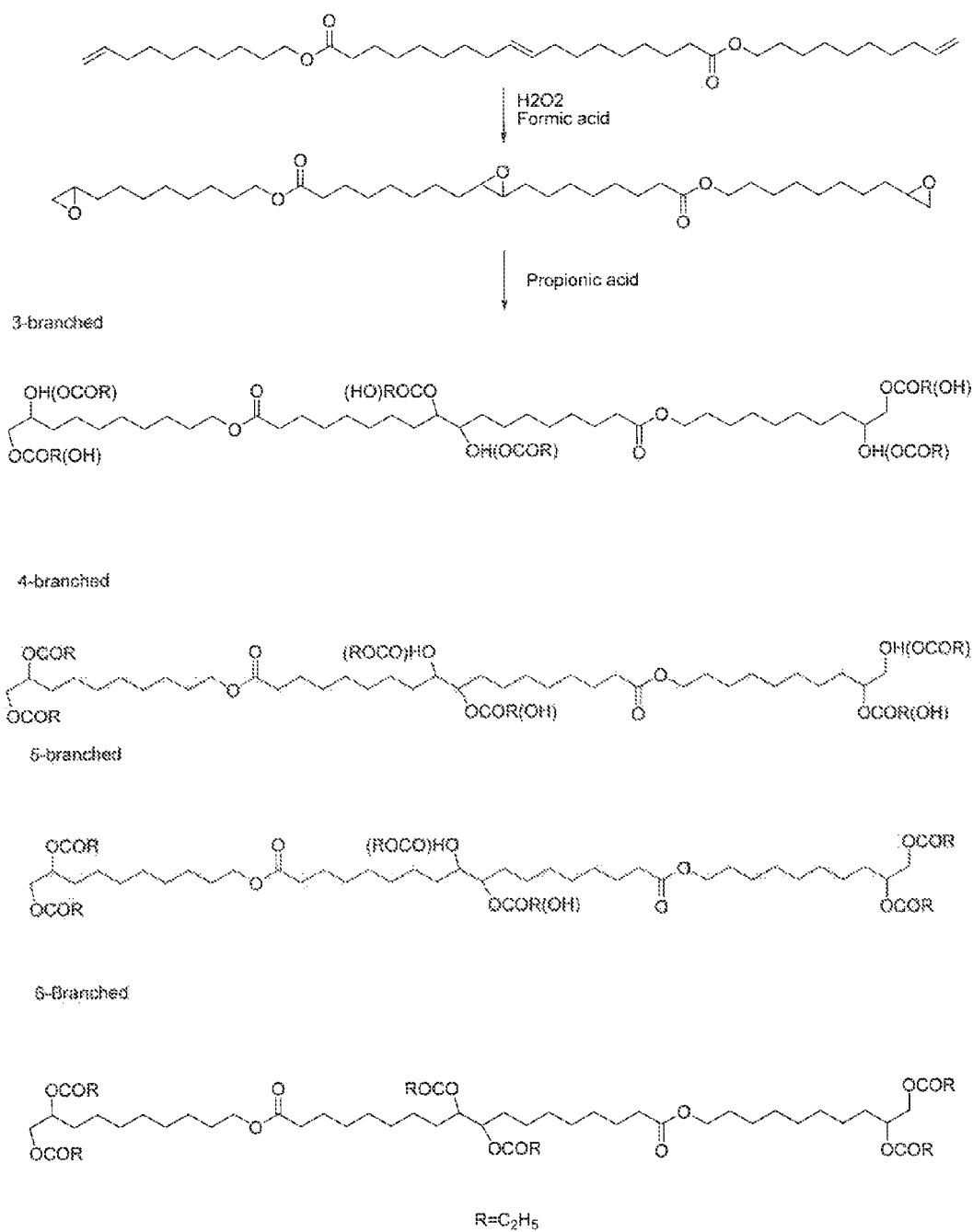
Figure 14: Synthesis of Compound H branched derivatives

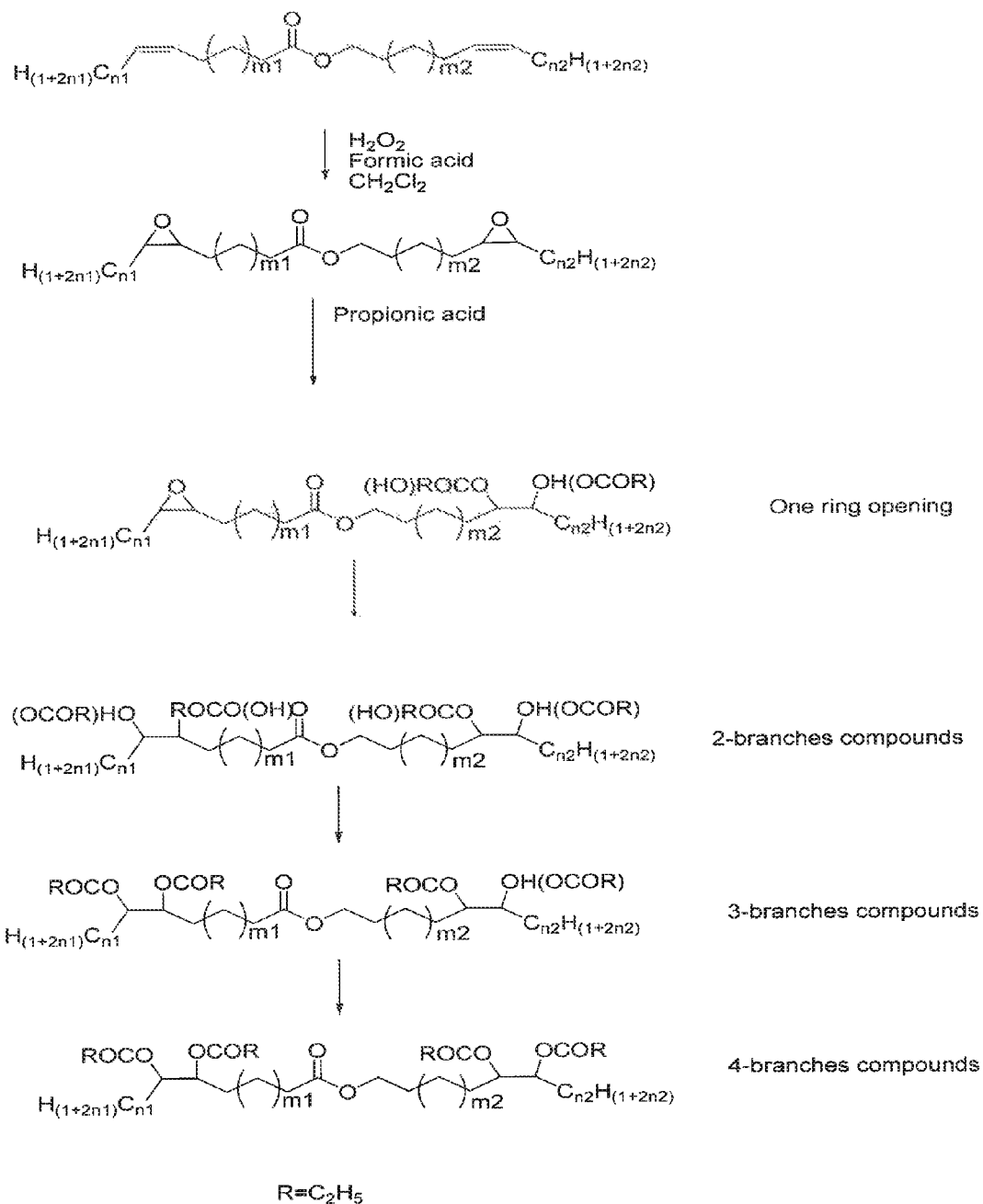
Figure 15: Synthesis of Branched Esters

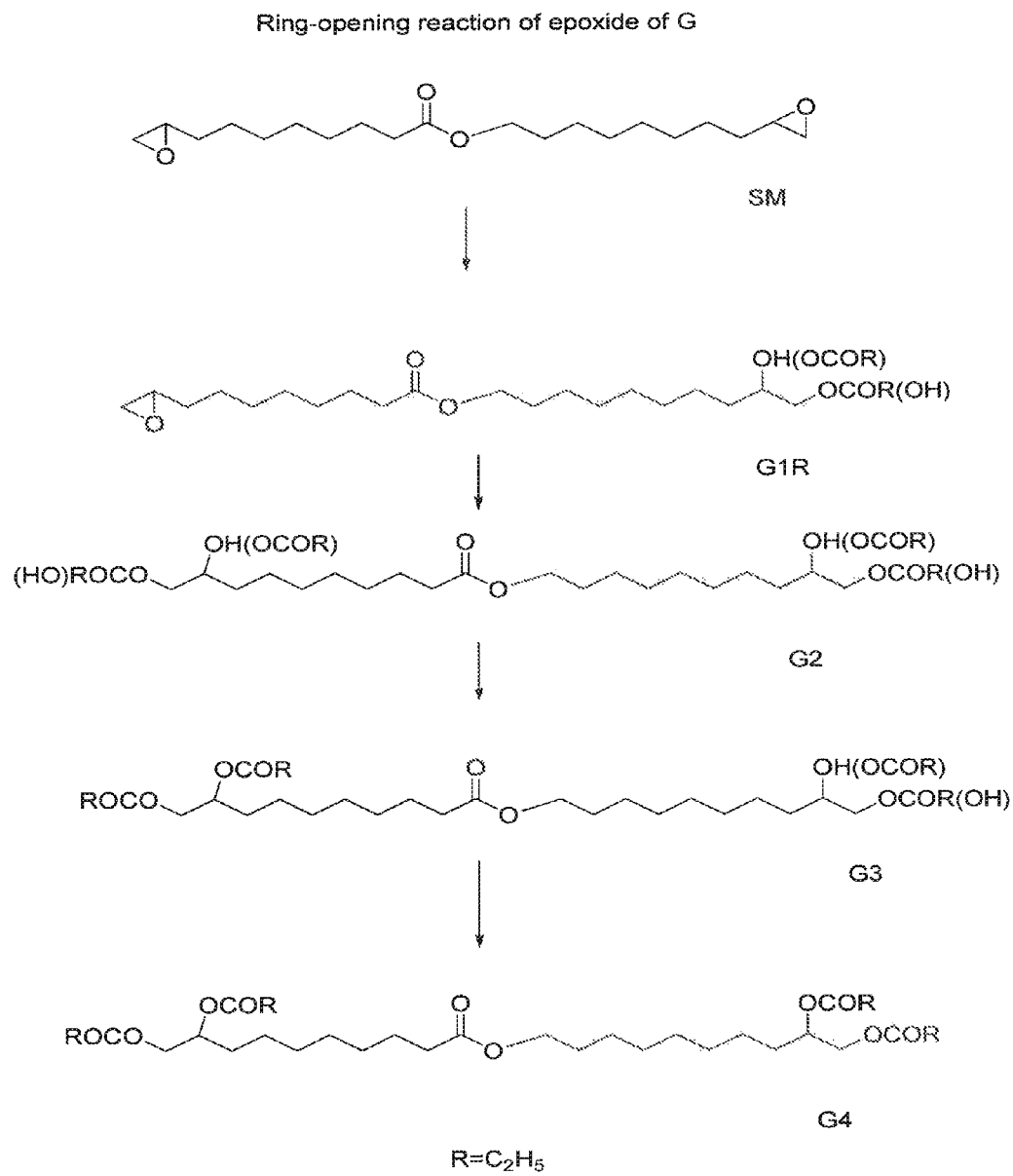
Figure 16: Ring-opening reaction of Epoxide of Compound G

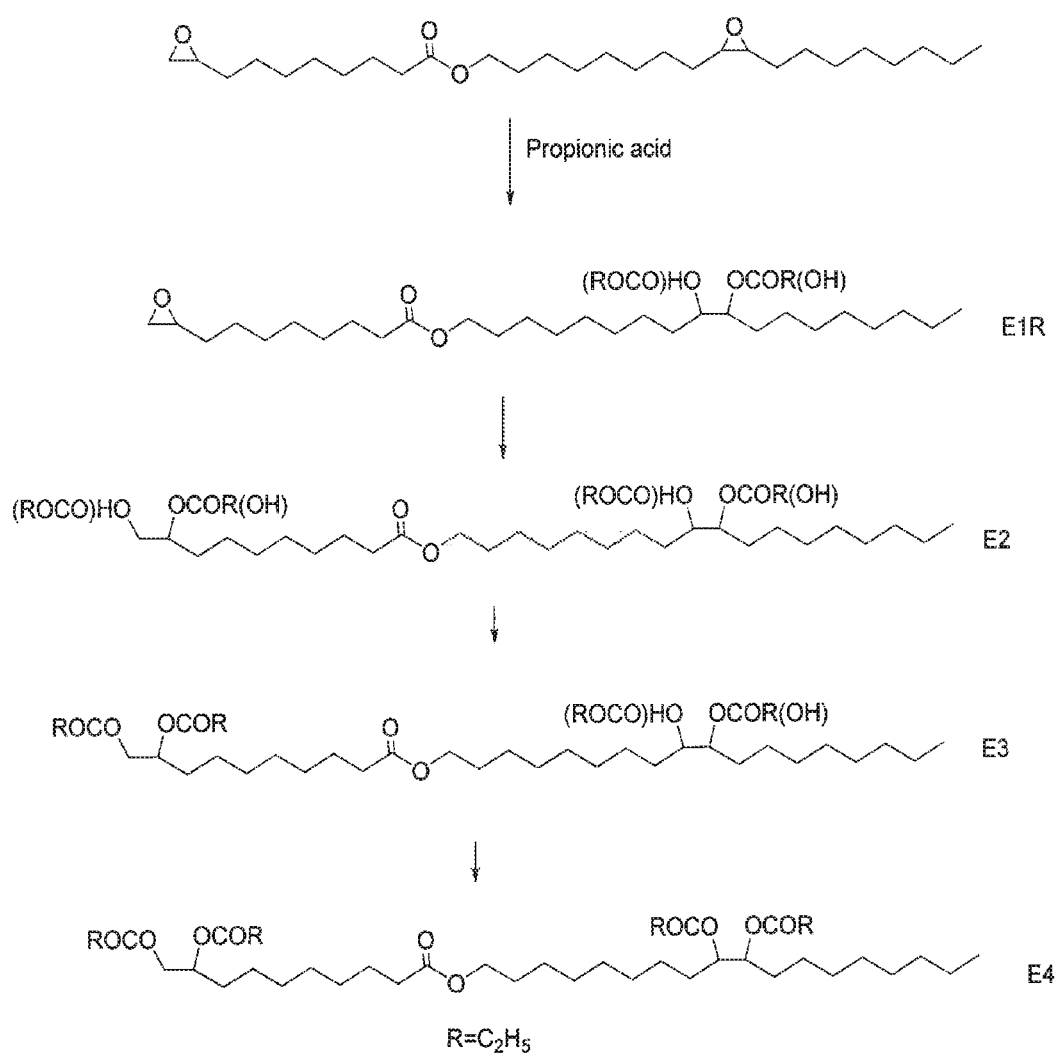
Figure 17: Ring-opening reaction of Epoxide of Compound E

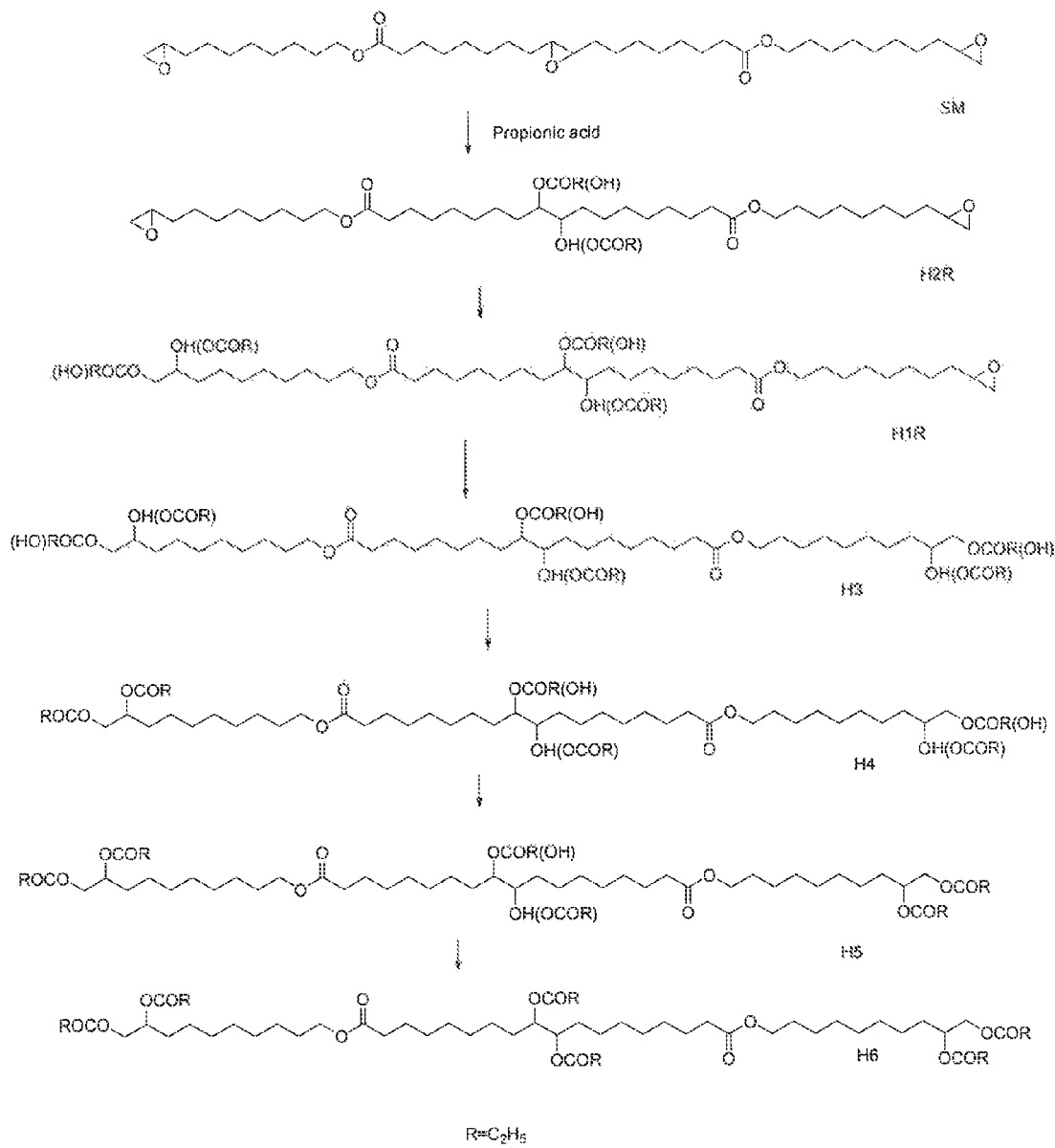
Figure 18: Ring-opening reaction of Epoxide of Compound H

ESTERS FOR USE AS A BASE STOCK AND IN LUBRICANT APPLICATIONS

FIELD OF THE INVENTION

This application relates to base ester compounds and complex ester compounds that can be used as a base stock or a base stock blend component for use in lubricant applications, and methods of making the same.

BACKGROUND OF THE INVENTION

Lubricants are widely used to reduce friction between surfaces of moving parts and thereby reduce wear and prevent damage to such surfaces and parts. Lubricants are composed primarily of a base stock and one or more lubricant additives. The base stock is generally a relatively high molecular weight hydrocarbon. In applications where there is a large amount of pressure applied to moving parts, lubricating compositions composed only of hydrocarbon base stock tend to fail and the parts become damaged. To make lubricants, such as motor oils, transmission fluids, gear oils, industrial lubricating oils, metal working oils, etc., one starts with a lubricant grade of petroleum oil from a refinery, or a suitable polymerized petrochemical fluid. Into this base stock, small amounts of additive chemicals are blended therein to improve material properties and performance, such as enhancing lubricity, inhibiting wear and corrosion of metals, and retarding damage to the fluid from heat and oxidation. As such, various additives such as oxidation and corrosion inhibitors, dispersing agents, high pressure additives, anti-foaming agents, metal deactivators and other additives suitable for use in lubricant formulations, can be added in conventional effective quantities. It has long been known that synthetic esters can be used both as a base stock and as an additive in lubricants. By comparison with the less expensive, but environmentally less safe mineral oils, synthetic esters were mostly used as base oils in cases where the viscosity/temperature behavior was expected to meet stringent demands. The increasingly important issues of environmental acceptance and biodegradability are the drivers behind the desire for alternatives to mineral oil as a base stock in lubricating applications. Synthetic esters may be polyol esters, polyalphaolefins (PAO), and triglycerides found in natural oils. Of key importance to natural oil derived lubricants are physical properties, such as improved low temperature properties, improved viscosity at the full range of operating conditions, improved oxidative stability (meaning removal of double bonds in the case of natural oil derived materials), and improved thermal stability.

Various prior art efforts have attempted to describe esters for use in biolubricant applications, examples of which include U.S. Patent Application No. 2009/0198075 titled Synthesis of Diester Based Biolubricants from Epoxides ("Ref. 1"); Synthesis and Physical Properties of Potential Biolubricants Based on Ricinoleic Acid, by Linxing Yao et al., *Journal of the American Oil Chemists' Society* 87, 2010: 937-945 ("Ref. 2"); Melting Points and Viscosities of Fatty Acid Esters that are Potential Targets for Engineered Oilseed, by Linxing Yao et al., *Journal of the American Oil Chemists' Society* 85, 2008,:77-82 ("Ref. 3"); Diesters from Oleic Acid: Synthesis, Low Temperature Properties and Oxidation Stability, by Bryan R. Moser et al. *Journal of the American Oil Chemists' Society* 84, 2007,:675-680 ("Ref. 4"); Oleic Acid Diesters Synthesis, Characterization and Low-Temperature Properties, by Jumat Salimon et al., *European Journal of Scientific Research* 32(2), 2009, 216-229 ("Ref. 5"); U.S. Pat. No. 6,018,063 titled Biodegradable Oleic Estolide Ester Base Stocks and Lubricants ("Ref. 6"); and Oleins as a Source of Estolides for Biolubricant Applications, by L. A. Garcia-Zapateiro et. al., *Grasas Y Aceites*, 61(2), 2010, 171-174 ("Ref. 7") (collectively, the "cited prior art"). However, none of the cited prior art references describe improved physical properties to the broad extent of the present invention.

SUMMARY OF THE INVENTION

In one aspect of the invention, a lubricant base stock composition is disclosed, comprising a complex ester having the formula (I):

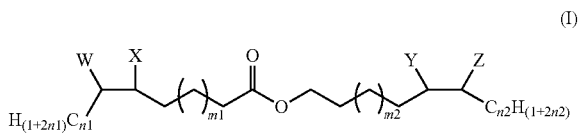

wherein n1=between 0 and 8; wherein n2=between 0 and 8; wherein m1=between 5 and 9; wherein m2=between 5 and 9; wherein W=OH or OCOR; wherein X=OH or OCOR; wherein Y=OCOR or OH; wherein Z=OH or OCOR; and in groups W, X, Y, and Z, R=CiHj, wherein i is 2 or greater and j is 5 or greater.

In another aspect of the invention, a lubricant base stock composition is disclosed comprising a complex ester having the formula (II):

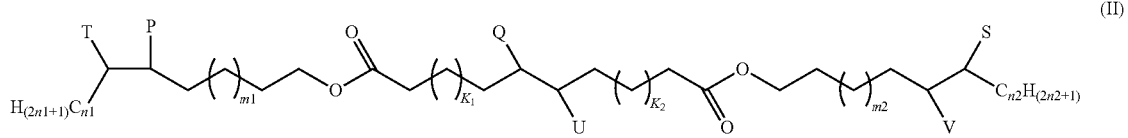

wherein n1=between 0 and 8; wherein n2=between 0 and 8; wherein m1=between 5 and 9; wherein m2=between 5 and 9; wherein k1=k2=5 or greater; wherein P=OH or OCOR; wherein Q=OH or OCOR; wherein S=OCOR or OH; wherein T=OH or OCOR; wherein U=OH or OCOR; wherein V=OH or OCOR, and in groups P, Q, S, T, U, and V, R=CiHj, wherein i is 2 or greater and j is 5 or greater.

In another aspect of the invention, a process for preparing a complex ester is disclosed, comprising the steps of: (a) reacting a fatty carboxylic acid having from between about 3 to 36 carbon atoms and a fatty alcohol having between about 8 to about 24 carbon atoms, in the presence of a base, a condensing agent, and a solvent, at temperature between about 4 and 50° C. for about 4 to 36 hours, to produce a base ester; (b) epoxidizing the base ester with a peroxyacid and a solvent at temperature between about 4 and 50° C. for about 4 to 36 hours to produce an epoxide; (c) reacting the epoxide with another fatty carboxylic acid having from between about 3 to 36 carbon atoms, at temperatures between about 50 and 150° C. for about 4 to 36 hours in a nitrogenous atmosphere, to produce said complex ester.

In another aspect of the invention, a process for preparing a complex ester comprising the steps of: (a) reacting a fatty carboxylic acid having from between about 3 to 36 carbon atoms and a metathesis catalyst, at temperature between about 30 and 70° C. for about 4 to 36 hours, then purified via a solvent to produce a diacid product; (b) reacting said diacid product with fatty alcohol having between about 8 to about 24 carbon atoms, in the presence of a base, a condensing agent, and a solvent, at a temperature between about 4 and 50° C. for about 4 to 36 hours, to produce a base ester; (b) epoxidizing the base ester with a peroxyacid and a solvent at temperature between about 4 and 50° C. for about 4 to 36 hours to produce an epoxide; (c) reacting the epoxide with another fatty carboxylic acid having from between about 3 to 36 carbon atoms, at temperatures between about 50 and 150° C. for about 4 to 36 hours in a nitrogenous atmosphere, to produce said complex ester.

In another aspect of the invention, a lubricant base stock composition is disclosed comprising a base ester having the formula (III):

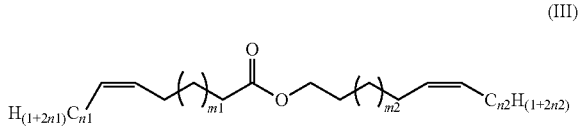

(III)

wherein n1=between 0 and 8; wherein n2=between 0 and 8; wherein m1=between 5 and 9; and wherein m2=between 5 and 9.

In another aspect of the invention, a lubricant base stock composition is disclosed comprising a base ester having the formula (IV):

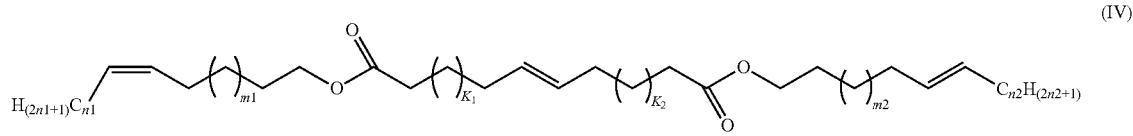

(IV)

wherein n1=between 0 and 8; wherein n2=between 0 and 8; wherein m1=between 5 and 9; wherein m2=between 5 and 9; and wherein k1=k2=5.

BRIEF DESCRIPTION OF THE DRAWINGS

FIG. 1 depicts the synthesis of dimer esters of the present invention.

FIG. 2 depicts a scheme for epoxidation of alkene of the present invention.

FIG. 3 depicts a scheme for the ring opening esterification of epoxides of the present invention.

FIG. 4 depicts the synthesis of dimer ester branched compounds of the present invention.

FIG. 4A depicts a generalized structure for the base dimer ester of the present invention.

FIG. 4B depicts a generalized structure for the dimer ester branched derivatives of the present invention.

FIG. 5 depicts the base trimer esters and their branched compounds of the present invention.

FIG. 5A depicts a generalized structure for the base trimer esters of the present invention.

FIG. 5B depicts a generalized structure for the trimer ester branched derivatives of the present invention.

FIG. 6 depicts the synthesis of Compound A and its branched derivatives of the present invention.

FIG. 7 depicts the synthesis of Compound B and its branched derivatives of the present invention.

FIG. 8 depicts the synthesis of Compound C and its branched derivatives of the present invention.

FIG. 9 depicts the synthesis of Compound D and its branched derivatives of the present invention.

FIG. 10 depicts the synthesis of Compound E and its branched derivatives of the present invention.

FIG. 11 depicts the synthesis of Compound F and its branched derivatives of the present invention.

FIG. 12 depicts the synthesis of Compound G and its branched derivatives of the present invention.

FIG. 13 depicts the synthesis of (E)-didec-9-enyl octadec-9-enedioate (Compound H) of the present invention.

FIG. 14 depicts the synthesis of Compound H branched derivatives of the present invention.

FIG. 15 depicts a general synthesis of branched esters of the present invention.

FIG. 16 depicts the ring-opening reaction of the epoxide of Compound G of the present invention.

FIG. 17 depicts the ring-opening reaction of the epoxide of Compound E of the present invention.

FIG. 18 depicts the ring-opening reaction of the epoxide of Compound H of the present invention.

DETAILED DESCRIPTION OF THE INVENTION

The present application relates to the compositions and methods for synthesis of base ester compounds and complex ester compounds for use as a base stock for lubricant applications, or a base stock blend component for use in a finished lubricant composition, or for particular applications. As used herein, base ester compounds may refer to dimer esters and/or trimer esters, where esters shall be understood to include mono-, di-, tri-, tetra-, and higher esters, as applicable. As used herein, complex esters refers to the respective branched derivatives of dimer esters, and/or the respective branched derivatives of trimer esters or diesters, or combinations of the respective branched derivatives of dimer esters and/or the respective branched derivatives of trimer esters and/or their respective branched derivatives. As used herein, the dimer esters, trimer esters or diesters, and the respective branched derivatives of either of these may at times be referred to generally as compounds, derivatives and/or samples.

The base esters and complex esters in accordance with the present invention may constitute a lubricant base stock composition, or a base stock blend component for use in a finished lubricant composition, or they may be mixed with one or more additives for further optimization as a finished lubricant or for a particular application. Suitable applications which may be utilized include, but are not limited to, two-cycle engine oils, hydraulic fluids, drilling fluids, greases, compressor oils, cutting fluids, milling fluids, and as emulsifiers for metalworking fluids. Suitable non-limiting examples of additives may include detergents, antiwear agents, antioxidants, metal deactivators, extreme pressure (EP) additives, dispersants, viscosity index improvers, pour point depressants, corrosion protectors, friction coefficient modifiers, colorants, antifoam agents, demulsifiers and the like. The base esters and complex esters in accordance with the present invention may also have alternative chemical uses and applications, as understood by a person skilled in the art. The content of the base esters and complex esters of the present invention will typically be present from about 0.1 to about 100% by weight, preferably about 25 to about 100% by weight, and most preferably from about 50 to about 100% by weight of a finished lubricant composition.

The dimer esters were prepared at room temperature (typically between 17-27° C.) by reacting a fatty carboxylic acid (or its acid halide, preferably an acid chloride created by reacting a fatty carboxylic acid with a chlorinating agent, such as thionyl chloride, phosphorus trichloride, oxalylchloride or phosphorus pentachloride) and a fatty alcohol with a condensing agent and a catalyst. The trimer esters, and in some embodiments, trimer diesters, were prepared, at room temperatures, by reacting an aliphatic dicarboxylic acid, preferably a diacid (or its acid halide, preferably an acid chloride created by reacting an aliphatic dicarboxylic acid with a chlorinating agent, such as thionyl chloride, phosphorus trichloride, or phosphorus pentachloride) with a fatty alcohol with a condensing agent and a catalyst. Also in some embodiments, the dimer and trimer esters may be prepared via a metathesis route.

The condensing agent typically is a carbodiimide, generally represented by the formula: $R^1N=C=NR^2$ wherein $R^1$ and $R^2$ are alkyl groups containing from 1 to about 18 carbon atoms, cycloalkyl groups containing 5 to about 10 carbon atoms and aryl groups, which term includes alkaryl and arylalkyl groups, containing 5 to about 18 carbon atoms. Non-limiting examples of such carbodiimides are dimethyl carbodiimide, diisopropyl carbodiimide, diisobutyl carbodiimide, dioctyl carbodiimide, tert-butyl isopropyl carbodiimide, dodecyl isopropyl carbodiimide, dicylohexyl carbodiimide, diphenyl carbodiimide, di-o-tolyl carbodiimide, bis(2,6-diethylphenyl) carbodiimide, bis(2,6-diisopropylphenyl carbodiimide, di-beta-naphthyl carbodiimide, benzyl isoopropyl carbodiimide, phenyl-o-tolyl carbodiimide and preferably, dicyclohexylcarbodiimide (DCC).

The catalyst may comprise a base, with non-limiting examples such as a triethyl amine, tripropyl amine, tributyl amine, pyridine and 4-dimethylamino pyridine or other pyridine derivative, and preferably, 4-dimethylaminopyridine (DMAP).

The solvent used in the esterification and/or epoxidation of the present invention may be chosen from the group including but not limited to aliphatic hydrocarbons (e.g., hexane and cyclohexane), organic esters (i.e. ethyl acetate), aromatic hydrocarbons (e.g., benzene and toluene), ethers (e.g., dioxane, tetrahydrofuran, ethyl ether, tert-butyl methyl ether), halogenated hydrocarbons (e.g., methylene chloride and chloroform), and preferably, chloroform.

The fatty carboxylic acid is derived from a natural oil, with non-limiting examples such as canola oil, rapeseed oil, coconut oil, corn oil, cottonseed oil, olive oil, palm oil, peanut oil, safflower seed oil, sesame seed oil, soybean oil, sunflower oil, linseed oil, palm kernel oil, tung oil, jojoba oil, jatropha oil, mustard oil, camellina oil, pennycress oil, hemp oil, algal oil, castor oil, lard, tallow, poultry fat, yellow grease, fish oil, tall oils, and mixtures thereof. Optionally, the natural oil may be partially and/or fully hydrogenated, and may also be refined, bleached, and/or deodorized. Suitable fatty carboxylic acids of natural oils include, but are not limited to, aliphatic, saturated, unsaturated, straight chain or branched fatty acids having 3 to 36 carbon atoms, such as propionic acid, caproic acid, caprylic acid, capric acid, caproleic acid (9-decenoic acid), lauric acid, nonanoic acid, myristic acid, palmitic acid, oleic acid, linoleic acid, linolenic acid, stearic acid, arachic acid, erucic acid and behenic acid.

The alcohol is typically a fatty alcohol of between 8 and 24 carbon atoms. The fatty alcohols are meant herein to include monohydric and polyhydric fatty alcohols, particularly those containing 8 to 24 carbon atoms exhibiting straight-chain or branched-chain structure, which are saturated or unsaturated (containing one or more carbon-carbon double bonds). Non-limiting examples of fatty alcohols include oleic, linolenic, linolenic, lauric, caproic, erucic, myristic and palmitic alcohols, as well as mixtures of any of the foregoing fatty alcohols. In some embodiments, the fatty alcohol may be an unsaturated primary alcohol such as 9-decen-1-ol, which is derived from 9-decenoic acid.

Following the above esterification, the base esters were epoxidized via any suitable peroxyacid. Peroxyacids (peracids) are acyl hydroperoxides and are most commonly produced by the acid-catalyzed esterification of hydrogen peroxide. Any peroxyacid may be used in the epoxidation reaction. The peroxyacids may be formed in-situ by reacting a hydroperoxide with the corresponding acid, such as formic or acetic acid. Examples of hydroperoxides that may be used include, but are not limited to, hydrogen peroxide, tert-butylhydroperoxide, triphenylsilylhydroperoxide, cumylhydroperoxide, and preferably, hydrogen peroxide. Other commercial organic peracids may also be used, such as benzoyl peroxide, and potassium persulfate. Commonly used solvents in the epoxidation of the present invention may be chosen from the group including but not limited to aliphatic hydrocarbons (e.g., hexane and cyclohexane), organic esters (i.e. ethyl acetate), aromatic hydrocarbons (e.g., benzene and toluene), ethers (e.g., dioxane, tetrahydrofuran, ethyl ether, tert-butyl methyl ether), halogenated hydrocarbons (e.g., methylene chloride and chloroform), and preferably, methylene chloride.

Following epoxidation, the addition of any suitable fatty carboxylic acids, typically having between 3 and 36 carbon atoms, preferably, propionic or nonanoic acid, was utilized to produce branched compounds, with further details as described later in this document.

In certain embodiments (compounds E, F, G, and H, and their branched derivatives), the fatty carboxylic acid derived from the natural oil may be metathesized in the presence of a metathesis catalyst. Metathesis is a catalytic reaction that involves the interchange of alkylidene units among compounds containing one or more double bonds (i.e., olefinic compounds) via the formation and cleavage of the carbon-carbon double bonds.

The metathesis catalyst in this reaction may include any catalyst or catalyst system that catalyzes a metathesis reaction. Any known metathesis catalyst may be used, alone or in combination with one or more additional catalysts. Non-limiting exemplary metathesis catalysts and process conditions are described in PCT/US2008/009635, pp. 18-47, incorporated by reference herein. A number of the metathesis catalysts as shown are manufactured by Materia, Inc. (Pasadena, Calif.).

With regards to compounds E, F, G, and H, and their branched derivatives, 9-decenoic acid may be formed by the cross-metathesis of oleic acid or methyl oleate, found in or derived from natural oils, with ethene, propene, butene, hexene, and/or a higher alpha-olefin which produces 9-decenoic acid (or the corresponding ester of decenoic acid if an ester (e.g., the methyl ester) of oleic acid is employed), and 1-decene. The cross-metathesis of oleic acid or methyl oleate with ethene, propene, butene and/or a higher alpha-olefin is carried out in the presence of a metathesis catalyst under suitable metathesis reaction conditions. Also, in some embodiments, compounds E, F, G and H may be prepared by cross-metathesis from compound A and an olefin having a terminal carbon double bond (such as those described in the preceding sentence). Generally, cross metathesis may be represented schematically as shown in Equation I:

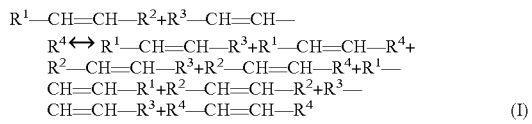

wherein $R^1$, $R^2$, $R^3$, and $R^4$ are organic groups.

In some embodiments, compound H may be prepared by self-metathesis via compound G (metathesis occurring between two of the same molecules, in this case, compound G). Generally, self-metathesis may be represented schematically as shown in Equation II below.

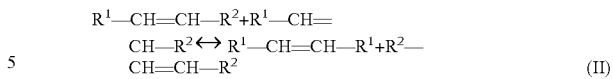

wherein $R^1$ and $R^2$ are organic groups.

In some embodiments, the 9-decenoic acid may be reduced to 9-decen-1-ol using a typical reducing agent under conditions known to a person skilled in the art. The reducing agent is typically a hydride reagent such as lithium aluminum hydride and boron hydrides such as sodium borohydride, diborane, and 9-borabicyclo[3.3.1]nonane (9-BBN); preferably, the reducing agent is lithium aluminum hydride. In the alternative, an ester of the 9-decenoic acid, such as methyl 9-decenoate, may be hydrogenated into 9-decen-1-ol with a hydrogen containing gas and in the presence of a catalyst system, under hydrogenation conditions known to a person skilled in the art. The 9-decen-1-ol may be reacted with a suitable fatty carboxylic acid or its acid chloride as stated below for specific compounds.

A non-limiting listing of representative dimer esters produced by the process of this invention is listed below in Table 1.

TABLE 1

Dimer Esters and their branched derivatives synthesized (the column headed "Structure" refers to the structures shown in FIGS. 1, 4, and 4A).

| Compounds | Name | Structure |
|---|---|---|
| A | Octadec-9-enoic acid octadec-9-enyl ester | $n1 = n2 = 8$<br>$m1 = m2 = 5$ |
| B | Docos-13-enoic acid octadec-9-enyl ester | $n1 = n2 = 8$<br>$m1 = 9; m2 = 5$ |
| C | Docos-13-enoic acid docos-13-enyl ester | $n1 = n2 = 8$<br>$m1 = m2 = 9$ |
| D | Octadec-9-enoic acid docos-13-enyl ester | $n1 = n2 = 8$<br>$m1 = 5; m2 = 9$ |
| E | octadec-9-enyl dec-9-enoate | $n1 = 0; n2 = 8$<br>$m1 = m2 = 5$ |
| F | dec-9-enyl oleate | $n1 = 8; n2 = 0$<br>$m1 = m2 = 5$ |
| G | dec-9-enyl dec-9-enoate | $n1 = n2 = 0$<br>$m1 = m2 = 5$ |
| A2 | 9(10)-hydroxy-10(9)-(propionyloxy)octadecyl 9(10)-hydroxy-10(9)-(propionyloxy)octadecanoate | $n1 = n2 = 8$<br>$m1 = m2 = 5$<br>$R = C_2H_5$ |
| A2-II | 9(10)-hydroxy-10(9)-(nonanoyloxy)octadecyl 9(10)-hydroxy-10(9)-(nonanoyloxy)octadecanoate | $n1 = n2 = 8$<br>$m1 = m2 = 5$<br>$R = C_8H_{17}$ |
| A3 | 1-(9(10)-hydroxy-10(9)-(propionyloxy)octadecanoyloxy)octadecane-9,10-diyldipropionate or/and 1-(9(10)-hydroxy-10(9)-(propionyloxy)octadecyloxy)-1-oxooctadecane-9,10-diyl dipropionate | $n1 = n2 = 8$<br>$m1 = m2 = 5$<br>$R = C_2H_5$ |
| A4 | 1-(9,10-bis(propionyloxy)octadecanoyloxy)octadecane-9,10-diyl dipropionate | $n1 = n2 = 8$<br>$m1 = m2 = 5$<br>$R = C_2H_5$ |
| B2 | 10(9)-hydroxy-9(10)-(propionyloxy)octadecyl 13(14)-hydroxy-14(13)-(propionyloxy)docosanoate | $n1 = n2 = 8$<br>$m1 = 9; m2 = 5$<br>$R = C_2H_5$ |
| B3 | 22-(10(9)-hydroxy-9(10)-(propionyloxy)octadecyloxy)-22-oxodocosane-9,10-diyl dipropionate or/and 1-(13(14)-hydroxy-14(13)-(propionyloxy)docosanoyloxy)octadecane-9,10-diyl dipropionate | $n1 = n2 = 8$<br>$m1 = 9; m2 = 5$<br>$R = C_2H_5$ |
| B4 | 1-(13,14-bis(propionyloxy)docosanoyloxy)octadecane-9,10-diyl dipropionate | $n1 = n2 = 8$<br>$m1 = 9; m2 = 5$<br>$R = C_2H_5$ |
| C2 | 13(14)-hydroxy-14(13)-(propionyloxy)docosyl 13(14)-hydroxy-14(13)-(propionyloxy)docosanoate | $n1 = n2 = 8$<br>$m1 = m2 = 9$<br>$R = C_2H_5$ |

TABLE 1-continued

Dimer Esters and their branched derivatives synthesized (the column headed "Structure" refers to the structures shown in FIGS. 1, 4, and 4A).

| Compounds | Name | Structure |
|---|---|---|
| C2-II | 13(14)-hydroxy-14(13)-(nonanoyloxy)docosyl 13(14)-hydroxy-14(13)-(nonanoyloxy)docosanoate | $n1 = n2 = 8$<br>$m1 = m2 = 9$<br>$R = C_8H_{17}$ |
| C3 | 22-(13(14)-hydroxy-14(13)-(propionyloxy)docosyloxy)-22-oxodocosane-9,10-diyl dipropionate or/and 22-(13(14)-hydroxy-14(13)-(propionyloxy)docosanoyloxy)docosane-9,10-diyl dipropionate | $n1 = n2 = 8$<br>$m1 = m2 = 9$<br>$R = C_2H_5$ |
| C4 | 22-(13,14-bis(propionyloxy)docosanoyloxy)docosane-9,10-diyl dipropionate | $n1 = n2 = 8$<br>$m1 = m2 = 9$<br>$R = C_2H_5$ |
| D2 | 14(13)-hydroxy-13(14)-(propionyloxy)docosyl 9(10)-hydroxy-10(9)-(propionyloxy)octadecanoate | $n1 = n2 = 8$<br>$m1 = 5; m2 = 9$<br>$R = C_2H_5$ |
| D3 | 22-(9(10)-hydroxy-10(9)-(propionyloxy)octadecanoyloxy)docosane-9,10-diyl dipropionate or/and 1-(14(13)-hydroxy-13(14)-(propionyloxy)docosyloxy)-1-oxooctadecane-9,10-diyl dipropionate | $n1 = n2 = 8$<br>$m1 = 5; m2 = 9$<br>$R = C_2H_5$ |
| D4 | 1-(13,14-bis(propionyloxy)docosyloxy)-1-oxooctadecane-9,10-diyl dipropionate | $n1 = n2 = 8$<br>$m1 = 5; m2 = 9$<br>$R = C_2H_5$ |
| E2-1 | 10(9)-hydroxy-9(10)-(propionyloxy)octadecyl 9-hydroxy-10-(propionyloxy)decanoate | $n1 = 0; n2 = 8$<br>$m1 = m2 = 5$<br>$R = C_2H_5$ |
| E2-2 | 10(9)-hydroxy-9(10)-(propionyloxy)octadecyl 10-hydroxy-9-(propionyloxy)decanoate | $n1 = 0; n2 = 8$<br>$m1 = m2 = 5$<br>$R = C_2H_5$ |
| E3 | 10-(10(9)-hydroxy-9(10)-(propionyloxy)octadecyloxy)-10-oxodecane-1,2-diyl dipropionate | $n1 = 0; n2 = 8$<br>$m1 = m2 = 5$<br>$R = C_2H_5$ |
| E4 | 1-(9,10-bis(propionyloxy)decanoyloxy)octadecane-9,10-diyl dipropionate | $n1 = 0; n2 = 8$<br>$m1 = m2 = 5$<br>$R = C_2H_5$ |
| F2-1 | 9-hydroxy-10-(propionyloxy)decyl 9(10)-hydroxy-10(9)-(propionyloxy)octadecanoate | $n1 = 8; n2 = 0$<br>$m1 = m2 = 5$<br>$R = C_2H_5$ |
| F2-2 | 10-hydroxy-9-(propionyloxy)decyl 9(10)-hydroxy-10(9)-(propionyloxy)octadecanoate | $n1 = 8; n2 = 0$<br>$m1 = m2 = 5$<br>$R = C_2H_5$ |
| F3 | 10-(9(10)-hydroxy-10(9)-(propionyloxy)octadecanoyloxy)decane-1,2-diyl dipropionate | $n1 = 8; n2 = 0$<br>$m1 = m2 = 5$<br>$R = C_2H_5$ |
| F4 | 1-(9,10-bis(propionyloxy)decyloxy)-1-oxooctadecane-9,10-diyl dipropionate | $n1 = 8; n2 = 0$<br>$m1 = m2 = 5$<br>$R = C_2H_5$ |
| G2-1 | 9-hydroxy-10-(propionyloxy)decyl 9-hydroxy-10-(propionyloxy)decanoate | $n1 = n2 = 0$<br>$m1 = m2 = 5$<br>$R = C_2H_5$ |
| G2-2 | 10-hydroxy-9-(propionyloxy)decyl 9-hydroxy-10-(propionyloxy)decanoate or/and 9-hydroxy-10-(propionyloxy)decyl 10-hydroxy-9-(propionyloxy)decanoate | $n1 = n2 = 0$<br>$m1 = m2 = 5$<br>$R = C_2H_5$ |
| G3-1 | 10-(9-hydroxy-10-(propionyloxy)decanoyloxy)decane-1,2-diyl dipropionate or/and 10-(9-hydroxy-10-(propionyloxy)decyloxy)-10-oxodecane-1,2-diyl dipropionate | $n1 = n2 = 0$<br>$m1 = m2 = 5$<br>$R = C_2H_5$ |
| G3-2 | 10-(10-hydroxy-9-(propionyloxy)decanoyloxy)decane-1,2-diyl dipropionate or/and 10-(10-hydroxy-9-(propionyloxy)decyloxy)-10-oxodecane-1,2-diyl dipropionate | $n1 = n2 = 0$<br>$m1 = m2 = 5$<br>$R = C_2H_5$ |
| G4 | 10-(9,10-bis(propionyloxy)decanoyloxy)decane-1,2-diyl dipropionate | $n1 = n2 = 0$<br>$m1 = m2 = 5$<br>$R = C_2H_5$ |

TABLE 2

Trimer Esters and their branched derivatives synthesized (the column headed "Structure" refers to the structures shown in FIGS. 5 and 5A).

| Compounds | Name | Structure |
|---|---|---|
| H | E-didec-9-enyl octadec-9-enedioate | $n1 = n2 = 0$; $m1 = m2 = 5$; $k1 = k2 = 5$ |
| H3 | 1-(9(10)-hydroxy-10(9)-(propionyloxy)decyl) 18-(10(9)-hydroxy-9(10)-(propionyloxy)-decyl)-9(10)-hydroxy-10(9)-(propionyloxy)-octadecanedioate | $n1 = n2 = 0$; $m1 = m2 = 5$; $k1 = k2 = 5$ $R = C_2H_5$ |
| H4 | 1-(9,10-bis(propionyloxy)decyl) 18-(9(10)-hydroxy-10(9)-(propionyloxy)decyl) 10(9)-hydroxy-9(10)-(propionyloxy)-octadecanedioate | $n1 = n2 = 0$; $m1 = m2 = 5$; $k1 = k2 = 5$ $R = C_2H_5$ |
| H5 | Bis (9,10-bis(propionyloxy)decyl)9(10)-hydroxy-10(9)-(propionyloxy)octadecandioate | $n1 = n2 = 0$; $m1 = m2 = 5$; $k1 = k2 = 5$ $R = C_2H_5$ |
| H6 | Bis (9,10-bis(propionyloxy)decyl)9,10-bis(propionyloxy)octadecanedioate | $n1 = n2 = 0$; $m1 = m2 = 5$; $k1 = k2 = 5$ $R = C_2H_5$ |

The dimer esters presented were prepared by two general procedures described in FIG. 1, with specifics described for each compound A-G described later below:

Procedure 1: To a solution of fatty alcohol (typically 1-100 mmol, preferably 5-50 mmol, and most preferably, 10 mmol) in Chloroform (typically 1-100 mL, preferably 10-50 mL, and most preferably, 20 mL), fatty acid (typically 1-100 mmol, preferably 5-50 mmol, and most preferably 10.1 mmol), 4-dimethylaminopyridine (typically 1-100 mmol, preferably 5-50 mmol, and most preferably 10 mmol) was added. To this reaction mixture in an ice bath, dicyclohexylcarbodiimide (typically 1-100 mmol, preferably 5-50 mmol, and most preferably 11 mmol) in Chloroform was added slowly and the reaction was stirred at a temperature (typically between 4-50° C., preferably between 12-33° C., and most preferably between 17-27° C.) overnight. The precipitated dicyclohexylurea was removed by filtration. The organic phase was then washed sequentially with water, 5% HCl, 4% NaHCO$_3$, water. The solvents were roto-evaporated and the residue was purified by column chromatography with Ethyl Acetate/Hexane to give a colorless oil.

Procedure 2: To a solution of fatty alcohol (typically 1-100 mmol, preferably 5-50 mmol, and most preferably 10 mmol) in chloroform (typically 1-100 mL, preferably 10-50 mL, and most preferably 30 mL), acyl chloride (typically 1-100 mmol, preferably 5-50 mmol, and most preferably 10 mmol) was added. Pyridine (typically 1-100 mmol, preferably 5-50 mmol, and most preferably 12 mmol) was then added to the reaction solution drop wise. The reaction mixture was stirred at a temperature (typically between 4-50° C., preferably between 12-33° C., and most preferably between 17-27° C.) overnight. The reaction mixture was then diluted with another amount of Chloroform (typically 1-300 mL, preferably 100-200 mL, and most preferably 160 mL). The organic layer was washed with water (3×50 mL), followed by 5% HCl (2×50 mL), water (2×50 mL), 4% NaHCO$_3$ (2×50 mL) and water (3×50 mL). The organic layer was dried over Na$_2$SO$_4$. After chloroform was removed, the residue was purified by column chromatography with Ethyl acetate/Hexane to give a colorless oil.

The synthesis of the esters were followed by epoxidation with peroxyacid which was formed from formic acid and hydrogen peroxide in situ to give epoxides (FIG. 2) with CH$_2$Cl$_2$ (methylene chloride) used as solvent. Compared to the reaction without CH$_2$Cl$_2$, epoxidation with CH$_2$Cl$_2$ as a solvent was faster with fewer side-products, since CH$_2$Cl$_2$ improves the solubility of the reagents in the reaction. Epoxidations of compounds E, F and G, with terminal double bonds, were slower (~36 hours as opposed to ~5 hours for the epoxidations of compounds A, B, C and D) because the alkyl group on the carbon double bond in compounds A, B and C can increase the rate of epoxidation.

To a stirred solution of ester (typically 1-100 mmol, preferably 5-50 mmol, and most preferably 10 mmol) and formic acid (typically 1-100 mmol, preferably 20-80 mmol, and most preferably 60 mmol) in CH$_2$Cl$_2$ (typically 1-100 mL, preferably 5-50 mL, and most preferably 10 mL) at 4° C., H$_2$O$_2$ (typically 1-100 mmol, preferably 5-70 mmol, and most preferably 44 mmol) was slowly added. The reaction proceeded at a temperature (typically between 4-50° C., preferably between 12-33° C., and most preferably between 17-27° C.) with vigorous stirring for 4-36 hrs. After removal of the aqueous phase, additional CH$_2$Cl$_2$ (30 mL) was added to the organic phase, which was washed sequentially with water (2×20 mL), saturated aqueous NaHCO$_3$ (2×10 mL) and brine (2×20 mL), then dried on Na$_2$SO$_4$, filtered, and concentrated. The residue was purified by column chromatography with Ethyl acetate/Hexane to give white crystals.

I. Synthesis of Dimer and Trimer Esters and Branched Derivatives of Dimer and Trimer Esters The addition of carboxylic acids to the epoxides by ring-opening esterification was accomplished to give branched compounds without need for either a further catalyst or further solvent as shown in FIGS. 2 and 3. The reactions with 2-branched compounds as main products were carried out at typically between 50-150° C., preferably between about 70-120° C., and most preferably at about 95° C., but those with 3- and 4-branched compounds were carried out at typically between 60-160° C., preferably between about 80-140° C., and most preferably at about 120° C., where water produced in the reactions was partially removed.

For branched compounds derived from compounds A, B, C and D, no effort to distinguish the regiochemistry (9-alkanonate-10-hydroxy-oactadecanoate versus the equally likely alkyl 10-alkanoate-9-9hydroxyoctadecanoate regio-isomer) or the stereochemistry (S, or R at C9 and C10) of the polyol esters was made due to the laborious chromatography required and the economics involved at potentially larger commercial scales. However, for those branched compounds derived from compounds E, F and G, in consideration of the fact that the position of hydroxyl group or carboxyl acid branch at the chain end would have significant influence on their properties, and since the differences in their polarity makes them easier to separate, the regio-isomers (but not stereo-isomers) were separated.

To the epoxidation products above, (typically 1-100 mmol, preferably 5-50 mmol, and most preferably 10 mmol), propionic acid or nonanoic acid (typically 1-400 mmol, preferably 100-300 mmol, and most preferably 220 mmol) was added. The reaction was carried out under an N$_2$ atmosphere and heated to typically between 50-150° C., preferably between about 70-120° C., and most preferably at 95° C. and stirred at 95° C. for typically between about 4 to 36 hours, preferably 10-20 hours, and most preferably 16 hours. To achieve 3 or 4 branches in the compounds, the reaction temperature was raised to typically between 60-160° C., preferably between about 80-140° C., and most preferably at 120° C. The resulting products were poured into 200 mL of water and extracted with Ethyl acetate (2×50 mL). The organic phase was washed sequentially by water (2×100 mL), saturated aqueousNaHCO$_3$ (2×100 mL) and brine (2×200 mL), dried on Na$_2$SO$_4$, and concentrated. The residue was purified by column chromatography with Ethyl Acetate/Hexane.

The dimer ester branched derivatives were prepared by the synthesis shown in FIG. 4. The respective dimer esters are depicted by the generalized structure in FIG. 4A, wherein n1=between 0 and 8; wherein n2=between 0 and 8; wherein m1=between 5 and 9; and wherein m2=between 5 and 9.

In a generalized manner, the syntheses of the dimer ester branched compounds yields a compound as depicted in FIG. 4B, wherein n1 is between 0 and 8; wherein n2 is between 0 and 8; wherein m1 is between 5 and 9; wherein m2 is between 5 and 9; wherein W is OH or OCOR; wherein X is OH or OCOR; wherein Y is OCOR or OH; wherein Z is OH or OCOR; and in groups W, X, Y, and Z, R=CiHj, wherein i is 2 or greater and j is 5 or greater.

The trimer esters presented (Compound H) and its branched derivatives are depicted as shown in FIG. 5. The respective base trimer ester is depicted by the generalized structure in FIG. 5A, wherein n1=between 0 and 8; wherein n2=between 0 and 8; wherein m1=between 5 and 9; wherein m2=between 5 and 9; and wherein k1=k2=5.

In a generalized manner, the syntheses of the trimer ester branched compounds yields a compound as depicted in FIG. 5B, wherein n1 is between 0 and 8; wherein n2 is between 0 and 8; wherein m1 is between 5 and 9; wherein m2 is between 5 and 9; wherein k1=k2=5 or greater; wherein P=OH or OCOR; wherein Q =OH or OCOR; wherein S=OCOR or OH; wherein T=OH or OCOR; wherein U=OH or OCOR; wherein V=OH or OCOR, and in groups P, Q, S, T, U, and V, R=CiHj, wherein i is 2 or greater and j is 5 or greater.

The compounds presented in Table 1 and Table 2 above were characterized with a combination of nuclear magnetic resonance ($^1$H-NMR), high performance liquid chromatography (HPLC), and/or mass spectrometry (MS), as shown in Table 3 below.

TABLE 3

Characterization of Compounds

| Compounds | Characterization methods | | |
|---|---|---|---|
| | 1H-NMR | HPLC-Fid | MS |
| A | Yes | No | No |
| B | Yes | No | No |
| C | Yes | No | No |
| D | Yes | No | No |
| E | Yes | No | No |
| F | Yes | No | No |
| G | Yes | No | No |
| A2 | Yes | No | No |
| A2-II | Yes | No | No |
| A3 | Yes | No | No |
| A4 | Yes | No | No |
| B2 | Yes | No | No |
| B3 | Yes | No | No |
| B4 | Yes | No | No |
| C2 | Yes | No | No |
| C2-II | Yes | No | No |
| C3 | Yes | No | No |
| C4 | Yes | No | No |
| D2 | Yes | Yes | No |
| D3 | Yes | No | No |
| D4 | Yes | Yes | No |
| E2-1 | Yes | Yes | Yes |
| E2-2 | Yes | Yes | No |
| E3 | Yes | Yes | No |
| E4 | Yes | Yes | No |
| F2-1 | Yes | Yes | No |
| F2-2 | Yes | Yes | No |
| F3 | Yes | Yes | Yes |

TABLE 3-continued

Characterization of Compounds

| Compounds | Characterization methods | | |
|---|---|---|---|
| | 1H-NMR | HPLC-Fid | MS |
| F4 | Yes | Yes | Yes |
| G2-1 | Yes | Yes | No |
| G2-2 | Yes | No | Yes |
| G3-1 | Yes | Yes | Yes |
| G3-2 | Yes | No | No |
| G4 | Yes | Yes | No |
| H | Yes | No | No |
| H3 | Yes | Yes | Yes |
| H4 | Yes | Yes | Yes |
| H5 | Yes | Yes | Yes |
| H6 | Yes | Yes | Yes |

The synthesis of the individual dimer and trimer esters, their epoxides, and their branched derivatives, are provided below:

Octadec-9-enoic acid octadec-9-enyl ester
(Compound A)

Compound A was prepared from Oleoyl chloride and oleyl alcohol in the presence of pyridine following the general procedure discussed before and as shown in FIG. 6. Pure compound A was a colorless oil obtained by column chromatography with Ethyl acetate/Hexane=1:30. Reaction conditions for branched derivative compounds A2, A3, and A4 are also shown below.

Yield: 98.5%

1H-NMR in CDCl$_3$ (ppm): 5.4 (4, m), 4.1 (2, t), 2.3 (2, t), 2.1-2.0 (8, m), 1.7-1.56 (4, m), 1.44-1.20 (42, m), 0.86-0.76 (6, t)

Purity: >95%

Docos-13-enoic acid octadec-9-enyl ester
(Compound B)

Compound B was prepared from Erucic acid and Oleyl alcohol in the presence of DCC and DMAP following the general procedure discussed before and as shown in FIG. 7. Pure compound B was a colorless oil obtained by column chromatography with Ethyl acetate/Hexane=1:40. Reaction conditions for branched derivative compounds B2, B3, and B4 are also shown below.

Yield: 91.8%

1H-NMR in CDCl$_3$ (ppm), 5.4 (4, m), 4.1 (2, t), 2.3 (2, t), 2.1-2.0 (8, m), 1.7-1.56 (4, m), 1.44-1.20 (50, m), 0.86-0.76 (6, t)

Purity: >95%

Docos-13-enoic acid docos-13-enyl ester
(Compound C)

Compound C was prepared from Erucic acid and Erucic alcohol with presence of DCC and DMAP following the general procedure discussed before and as shown in FIG. 8. Pure compound C was a colorless oil obtained by column chromatography with Ethyl acetate/Hexane=1:40. Reaction conditions for branched derivative compounds C2, C3, and C4 are also shown below.

Yield: 95%

1H-NMR in CDCl$_3$ (ppm), 5.4 (4, m), 4.1 (2, t), 2.3 (2, t), 2.1-2.0 (8, m), 1.7-1.56 (4, m), 1.44-1.20 (58, m), 0.86-0.76 (6, t)

Purity:>95%

Octadec-9-enoic acid docos-13-enyl ester (Compound D)

Compound D was prepared from Oleoyl chloride and Erucic acid following the general procedure discussed before and as shown in FIG. 9. Pure compound D was a colorless oil obtained by column chromatography with Ethyl acetate/Hexane=1:40. Reaction conditions for branched derivative compounds D2, D3, and D4 are also shown below.

Yield: 94.5%
1H-NMR in $CDCl_3$ (ppm), 5.4 (4, m), 4.1 (2, t), 2.3 (2, t), 2.1-2.0 (8, m), 1.7-1.56 (4, m), 1.44-1.20 (50, m), 0.86-0.76 (6, t)
Purity:>95%

Octadec-9-enyl dec-9-enoate (Compound E)

Compound E was prepared from Oleyl alcohol and 9-decenoic acid following the general procedure previously discussed and shown in FIG. 10. Pure compound E was a colorless oil obtained by column chromatography with Ethyl acetate/Hexane=1:40.

Yield: 96%
1H-NMR in $CDCl_3$ (ppm), 5.8 (1, m), 5.4 (2, m), 5.0 (2, dd), 4.1 (2, t), 2.3 (2, t), 2.0 (6, m), 1.6 (4, m), 1.4-1.2 (30, m), 0.9 (3, t)
Purity:>95%

Dec-9-enyl oleate (Compound F)

Compound F was prepared from Oleoyl chloride and 9-decen-1-ol following the general procedure already discussed and shown in FIG. 11. Pure compound F was a colorless oil obtained by column chromatography with Ethyl acetate/Hexane=1:40.

Yield: 97.5%
1H-NMR in $CDCl_3$ (ppm), 5.8 (1, m), 5.4 (2, m), 5.0 (2, dd), 4.1 (2, t), 2.3 (2, t), 2.0 (6, m), 1.6 (4, m), 1.4-1.2 (30, m), 0.9 (6, t)
Purity:>95%

Dec-9-enyl dec-9-enoate (Compound G)

Compound G was prepared from 9-decen-1-ol and 9-decenoic acid following the general procedure already discussed and shown in FIG. 12. Pure compound G was a colorless oil by column chromatography with Ethyl acetate/Hexane=1:50.

Yield: 92.7%
1H-NMR in $CDCl_3$ (ppm), 5.8 (2, m), 5.0 (4, dd), 4.0 (2, t), 2.3 (2, t), 2.0 (4, m), 1.6 (4, m), 1.4-1.2 (18, m)
Purity:>95%

8-(3-octyloxiran-2-yl) octyl 8-(3-octyloxiran-2-yl) octanoate (Epoxides of A)

Epoxide was prepared from compound A with $H_2O_2$ and Formic acid as shown in FIG. 6. Pure compound was obtained by column chromatography with Ethyl acetate/Hexane=1:30.

Yield: 70%
1H-NMR in $CDCl_3$ (ppm): 4.1 (2, t), 2.9 (4, Br), 2.3 (2, t), 2.1-2.0 (8, m), 1.7-1.6 (4, m), 1.5-1.20 (42, m), 0.86-0.76 (6, t)
Purity:>95%

8-(3-octyloxiran-2-yl)octyl 12-(3-octyloxiran-2-yl) dodecanoate (Epoxide of B)

Epoxide was prepared from compound B with $H_2O_2$ and Formic acid with $CH_2Cl_2$ as a solvent as shown in FIG. 7. Pure compound was obtained by column chromatography with Ethyl acetate/Hexane=1:20.

Yield: 75%
1H-NMR in $CDCl_3$ (ppm), 4.1 (2, t), 2.9 (4, br), 2.3 (2, t), 2.1-2.0 (8, m), 1.7-1.56 (4, m), 1.44-1.20 (50, m), 0.86-0.76 (6, t)
Purity:>95%

12-(3-octyloxiran-2-yl)dodecyl 12-(3-octyloxiran-2-yl)dodecanoate (Epoxide of C)

Epoxide was prepared from compound C with $H_2O_2$ and Formic acid and the mixture of Hexane (20 mL) and Ethyl acetate (10 mL) as solvent (Shown in FIG. 8). Pure compound was obtained by column chromatography with Ethyl acetate/Hexane=1:20 as white solid.

Yield: 73%
1H-NMR in $CDCl_3$ (ppm), 4.1 (2, t), 2.9 (4, br), 2.3 (2, t), 2.1-2.0 (8, m), 1.7-1.56 (4, m), 1.44-1.20 (58, m), 0.86-0.76 (6, t)
Purity:>95%

12-(3-octyloxiran-2-yl)dodecyl 8-(3-octyloxiran-2-yl)octanoate (Epoxide of D)

Epoxide was prepared from compound D with $H_2O_2$ and Formic acid with $CH_2Cl_2$ as solvent (shown in FIG. 9). Pure compounds was obtained by column chromatography with Ethyl acetate/Hexane=1:30 as white solid.

Yield: 72.7%
1H-NMR in $CDCl_3$ (ppm), 4.1 (2, t), 2.9 (4, br), 2.3 (2, t), 2.1-2.0 (8, m), 1.7-1.56 (4, m), 1.44-1.20 (50, m), 0.86-0.76 (6, t)
Purity:>95%

8-(3-octyloxiran-2-yl)octyl 8-(oxiran-2-yl)octanoate (Epoxide of E)

Epoxide was prepared from compound E with $H_2O_2$ and Formic acid with $CH_2Cl_2$ as solvent and at room temperature for 28 hours (shown in FIG. 10). Pure compounds was obtained by column chromatography with Ethyl acetate/Hexane=1:10 as colorless oil.

Yield: 75.6%
1H-NMR in $CDCl_3$ (ppm), 4.1 (2, t), 2.9 (3, br), 2.8 (1, t), 2.5 (1, t) 2.3 (2, t), 1.6-1.2 (40, m), 0.9 (3, t)
Purity:>95%

8-(oxiran-2-yl)octyl 8-(3-octyloxiran-2-yl)octanoate (Epoxide of F)

Epoxide was prepared from compound F with $H_2O_2$ and Formic acid with $CH_2Cl_2$ as solvent and at room temperature for 48 hours (shown in FIG. 11). Pure compounds was obtained by column chromatography with Ethyl acetate/Hexane=1:10 as colorless oil.

Yield: 71.4%
1H-NMR in $CDCl_3$ (ppm), 4.1 (2, t), 2.9 (3, br), 2.8 (1, t), 2.5 (1, t) 2.3 (2, t), 1.6-1.2 (40, m), 0.9 (3, t)
Purity: >95%

8-(oxiran-2-yl)octyl 8-(oxiran-2-yl)octanoate (Epoxide of G)

Epoxide was prepared from compound F with $H_2O_2$ and Formic acid with $CH_2Cl_2$ as solvent and at room temperature for 48 hours (shown in FIG. 12). Pure compounds was obtained by column chromatography with Ethyl acetate/Hexane=1:10 as colorless oil.

Yield: 72%

1H-NMR in $CDCl_3$ (ppm), 4.0 (2, t), 3.0 (2, br), 2.7 (2, t), 2.5 (2, t), 2.3 (2, t), 1.6-1.2 (27, m)

Purity: >95%

Branched Derivatives of Compound A

Branched compound A derivatives were prepared from epoxide of compound A and propionic acid (or nonanoic acid for A2-II) at 95° C. for A2 and A3 or 120° C. for A3 and A4 (Shown in FIG. 6).

9(10)-hydroxy-10(9)-(propionyloxy)octadecyl 9(10)-hydroxy-10(9)-(propionyloxy) octadecanoate (A2)

Pure compound A2 was given as colorless oil by column chromatography with Ethyl acetate/Hexane=1:10.

Yield: 89.5%

1H-NMR in $CDCl_3$ (ppm), 4.8 (2, m), 4.1 (2, t), 3.7-3.5 (2,m), 2.4-2.2 (6, m), 1.5-1.2 (46, m), 1.1 (6, t), 0.8 (6, t)

Purity>95%

9(10)-hydroxy-10(9)-(nonanoyloxy)octadecyl 9(10)-hydroxy-10(9)-(nonanoyloxy)octadecanoate (A2-II)

Pure compound A2-II was given as colorless oil by column chromatography with Ethyl Acetate/Hexane=1:10.

Yield: 64%

1H-NMR in $CDCl_3$ (ppm), 4.8 (2, m), 4.1 (2, t), 3.7-3.5 (2,m), 2.4-2.2 (6, m), 1.6 (16, m), 1.5-1.2 (62, m), 0.8 (12, t)

Purity:>95%

1-(9(10)-hydroxy-10(9)-(propionyloxy)octadecanoyloxy)octadecane-9,10-diyldipropionate or/and 1-(9(10)-hydroxy-10(9)-(propionyloxy)octadecyloxy)-1-oxooctadecane-9,10-diyl dipropionate (A3)

Pure compound A3 was given as colorless oil by column chromatography with Ethyl acetate/Hexane=1:6.

Yield: 30.6% A4+38.2% A3 at 120° C.

1H-NMR in $CDCl_3$ (ppm), 5.0 (2, m), 4.8 (1, m), 4.0 (2, t), 3.6 (1, m), 2.4-2.2 (8, m), 1.8-1.2 (55, m), 1.1 (9, t), 0.8 (6, t)

Purity:>95%

1-(9,10-bis(propionyloxy)octadecanoyloxy)octadecane-9,10diyl dipropionate (A4)

Pure compound A4 was given as colorless oil by column chromatography with Ethyl acetate/Hexane=1:10.

Yield: 30.6% A4+38.2% A3 at 120° C.

1H-NMR in $CDCl_3$ (ppm), 5.0 (4, m), 4.0 (2, t), 2.4-2.2 (10, m), 1.7-1.5 (6, m), 1.4-1.2 (48, m), 1.1 (12, t), 0.8 (6, t)

Purity:>95%

Branched derivatives of Compound B

Branched Compound B derivatives were prepared from the epoxide of compound B and propionic acid at 95° C. for B2 and B3 or 120° C. for B3 and B4 (shown FIG. 7).

10(9)-hydroxy-9(10)-(propionyloxy)octadecyl 13(14)-hydroxy-14(13)-(propionyloxy)docosanoate (B2)

Pure compound B2 was given as colorless oil by column chromatography with Ethyl acetate/Hexane=1:8.

Yield: 47.8% B2+29% B3 at 95° C.; 46% B2+35.7% B3+11.3% B4 at 120° C.

1H-NMR in $CDCl_3$ (ppm), 4.8 (2, m), 4.0 (2, t), 3.6 (2, br), 2.3 (4, q), 2.2 (2, t), 1.8-1.5 (10, m), 1.5-1.2 (56, m), 1.1 (6, t), 0.8 (6, t)

Purity: >95%

22-(10(9)-hydroxy-9(10)-(propionyloxy)octadecyloxy)-22-oxodocosane-9,10diyl dipropionate or/and 1-(13(14)-hydroxy-14(13)-(propionyloxy) docosanoyloxy)octadecane-9,10diyl dipropionate (B3)

Pure compound B3 was given as colorless oil by column chromatography with Ethyl acetate/Hexane=1:10.

Yield: 47.8% B2+29% B3 at 95° C.; 46% B2+35.7% B3+11.3% B4 at 120° C.

1H-NMR in $CDCl_3$ (ppm), 5.0 (2, m), 4.8 (1, m), 4.0 (2, t), 3.6 (1, br), 2.4-2.2 (8, m), 1.7-1.2 (63, m), 1.1 (9, t), 0.8 (6, t)

Purity:>95%

1-(13,14-bis(propionyloxy)docosanoyloxy)octadecane-9,10diyl dipropionate (B4)

Pure compound B4 was given as colorless oil by column chromatography with Ethyl acetate/Hexane=1:10.

Yield: 46% B2+35.7% B3+11.3% B4 at 120° C.

1H-NMR in $CDCl_3$ (ppm), 4.8 (4, m), 3.6 (2, t), 2.2-2.0 (10, m), 1.4-1.2 (12, br), 1.1-0.9 (50, m), 0.8 (12, t), 0.6 (6, t)

Purity:>95%

Branched Derivatives of Compound C

Branched Compound C derivatives were prepared from epoxide of compound C and propionic acid (or nonanoic acid for C2-II) at 95° C. for compounds C2 and C3 or 120° C. for C3 and C4 (shown in FIG. 8).

13(14)-hydroxy-14(13)-(propionyloxy)docosyl 13(14)-hydroxy-14(13)-(propionyloxy)docosanoate (C2)

Pure compound C2 was given as colorless oil by column chromatography with Ethyl acetate/Hexane=1:8.

Yield: 71.6% C2 and 17.9% C3 at 95° C.

1H-NMR in $CDCl_3$ (ppm), 4.8 (2, m), 4.1 (2, t), 3.6 (2, br), 2.4 (4, q), 2.3 (2, t), 1.6 (10, br), 1.5-1.2 (62, m), 1.1 (6, t), 0.9 (6, t)

Purity:>95%

13(14)-hydroxy-14(13)-(nonanoyloxy)docosyl 13(14)-hydroxy-14(13)-(nonanoyloxy)docosanoate (C2-II)

Yield: 87.1%

1H-NMR in $CDCl_3$ (ppm), 4.8 (2, m), 4.1 (2, t), 3.6 (2, br), 2.4-2.3 (6, t), 1.6 (12, br), 1.5-1.2 (86, m), 0.9 (12, t)

Purity: >95%

22-(13(14)-hydroxy-14(13)-(propionyloxy)docosyloxy)-22-oxodocosane-9,10diyl dipropionate or/and 22-(13(14)-hydroxy-14(13)-(propionyloxy) docosanoyloxy)docosane-9,10diyl dipropionate (C3)

Pure compound C3 was given as colorless oil by column chromatography with Ethyl acetate/Hexane=1:10.
Yield: 71.6% C2 and 17.9% C3 at 95° C., 44.8% C4+39.7% C3 at 120° C.
1H-NMR in $CDCl_3$ (ppm), 5.0 (2, m), 4.8 (1, m), 4.0 (2, t), 3.5 (1, br), 2.4-0.22 (8, m), 1.6-1.2 (71,m), 1.1 (9, t), 0.8 (6, t)
Purity:>95%

22-(13,14-bis(propionyloxy)docosanoyloxy) docosane-9,10diyl dipropionate (C4)

Pure compound C4 was given as colorless oil by column chromatography with Ethyl acetate/Hexane=1:10.
Yield: 44.8% C4+39.7% C3 at 120° C.
1H-NMR in $CDCl_3$ (ppm), 5.0 (4, m), 4.0 (2, t), 2.4-2.2 (10, m), 1.6-1.4 (12, br), 1.4-1.2 (58, m), 1.1 (12, t), 0.8 (6, t)
Purity:>95%

Branched Derivatives of Compound D

Branched Compound D derivatives were prepared from the epoxide of compound D and propionic acid at 95° C. for D2 and D3 or 120° C. for D3 and D4 (shown in FIG. 9).

14(13)-hydroxy-13(14)-(propionyloxy)docosyl 9(10)-hydroxy-10(9)-(propionyloxy)octadecanoate (D2)

Pure compound D2 was given as colorless oil by column chromatography with Ethyl acetate/Hexane=1:8.
Yield: 77.8% D2+9.5% D3 at 95° C.
1H-NMR in $CDCl_3$ (ppm), 4.8 (2, m), 4.0 (2, t), 3.6 (2, br), 2.3 (4, q), 2.2 (2, t), 1.8-1.5 (10, m), 1.5-1.2 (54, m), 1.1 (6, t), 0.8 (6, t)
Purity:>95%

22-(9(10)-hydroxy-10(9)-(propionyloxy)octadecanoyloxy)docosane-9,10diyl dipropionate or/and 1-(14(13)-hydroxy-13(14)-(propionyloxy)docosyloxy)-1-oxooctadecane-9,10diyl dipropionate (D3)

Pure compound D3 was given as colorless oil by column chromatography with Ethyl acetate/Hexane=1:10.
Yield: 77.8% D2+9.5% D3 at 95° C., 42.8% D4+48.5% D3 at 120° C.
1H-NMR in $CDCl_3$ (ppm), 5.0 (2, m), 4.8 (1, m), 4.0 (2, t), 3.6 (1, br), 2.4-2.2 (8, m), 1.7-1.2 (63, m), 1.1 (9, t), 0.8 (6, t)
Purity:>95%

1-(13,14-bis(propionyloxy)docosyloxy)-1-oxooctadecane-9,10diyl dipropionate (D4)

Pure compound D4 was given as colorless oil by column chromatography with Ethyl acetate/Hexane=1:10.
Yield: 42.8% D4+48.5% D3 at 120° C.
1H-NMR in $CDCl_3$ (ppm), 4.8 (4, m), 3.6 (2, t), 2.2-2.0 (10, m), 1.4-1.2 (12, br), 1.1-0.9 (50, m), 0.8 (12, t), 0.6 (6, t)
Purity:>95%

Branched Derivatives of Compound E

Branched Compound E derivatives were prepared from the epoxide of compound E and propionic acid at 95° C. for E2 and E3 or 120° C. for E3 and E4 (shown in FIG. 10).

10(9)-hydroxy-9(10)-(propionyloxy)octadecyl 9-hydroxy-10-(propionyloxy)decanoate (E2-1)

Pure compound E2-1 was given as colorless oil by column chromatography with Ethyl acetate/Hexane=1:4.
Yield: 26% g E3+58% E2-M at 95° C. (E2-M meaning a 70:30 wt:wt mixture of E2-1 and E2-2 by HPLC).
1H-NMR in $CDCl_3$ (ppm), 5.0-4.8 (1, m), 4.2 (1, d), 4.1 (2, t), 4.0 (1, dd), 3.8 (1, m), 3.7-3.5 (2, m), 2.4 (4, m), 2.2 (2, t), 1.6-1.2 (41, m), 1.1 (6, m), 0.8 (3, t)
MS (+Na+), 623.7
Purity:>95%

10(9)-hydroxy-9(10)-(propionyloxy)octadecyl 10-hydroxy-9-(propionyloxy)decanoate (E2-2)

Pure compound E2-2 was given as colorless oil by column chromatography with Ethyl acetate/Hexane=1:4.
Yield: 26% g E3+58% E2-M at 95° C.
1H-NMR in $CDCl_3$ (ppm), 5.0-4.8 (1, m), 4.2 (1, d), 4.1 (2, t), 4.0 (1, dd), 3.8 (1, m), 3.7-3.5 (2, m), 2.4 (4, m), 2.2 (2, t), 1.6-1.2 (41, m), 1.1 (6, m), 0.8 (3, t)
Purity: 94.3%

10-(10(9)-hydroxy-9(10)-(propionyloxy)octadecyloxy)-10-oxodecane-1,2diyl dipropionate (E3)

Pure compound E3 was given as colorless oil by column chromatography with Ethyl acetate/Hexane=1:6 to 1:3.
Yield: 26% g E3+58% E2-M at 95° C., 32.5% E4+21.5% E3+33.7% E2 at 120° C.
1H-NMR in $CDCl_3$ (ppm), 5.1 (1, m), 4.8 (1, m), 4.2 (1, d), 4.0 (3, m), 3.6 (3, br), 2.3 (8, m), 1.7-1.2 (41, m), 1.1 (9, m), 0.8 (3, t)
Purity:>95%

1-(9,10-bis(propionyloxy)decanoyloxy)octadecane-9,10diyl dipropionate (E4)

Pure compound E4 was given as colorless oil by column chromatography with Ethyl acetate/Hexane=1:6.
Yield: 32.5% E4+21.5% E3+33.7% E2 at 120° C.
1H-NMR in $CDCl_3$ (ppm), 5.1 (1, m), 5.0 (2, m), 4.2 (1, d), 4.0 (3, m), 2.3 (10, m), 1.7-1.5 (10, m), 1.4-1.2 (30, m), 1.1 (12, m), 0.8 (3, t)
Purity:>95%

Branched Derivatives of Compound F

Branched Compound F derivatives were prepared from the epoxide of compound F and propionic acid at 95° C. for F2 and F3 or 120° C. for F3 and F4 (shown in FIG. 11).

9-hydroxy-10-(propionyloxy)decyl 9(10)-hydroxy-10(9)-(propionyloxy)octadecanoate (F2-1)

Pure compound F2-1 was given as colorless oil by column chromatography with Ethyl acetate/Hexane=1:4.
Yield: 19.8% F3+64.3% F2-M from 3.2 g
1H-NMR in $CDCl_3$ (ppm), 5.0-4.8 (1, m), 4.2 (1, d), 4.1 (2, t), 4.0 (1, dd), 3.8 (1, m), 3.7-3.5 (2, m), 2.4 (4, m), 2.2 (2, t), 1.6 (8, m), 1.6-1.2 (33, m), 1.1 (6, m), 0.8 (3, t)
Purity:>95%

10-hydroxy-9-(propionyloxy)decyl 9(10)-hydroxy-10(9)-(propionyloxy)octadecanoate (F2-2)

Pure compound F2-2 was given as colorless oil by column chromatography with Ethyl acetate/Hexane=1:4.
Yield: 19.8% F3+64.3% F2-M
1H-NMR in CDCl$_3$ (ppm), 5.0-4.8 (1, m), 4.2 (1, d), 4.1 (2, t), 4.0 (1, dd), 3.8 (1, m), 3.7-3.5 (2, m), 2.4 (4, m), 2.2 (2, t), 1.6 (8, m), 1.6-1.2 (33, m), 1.1 (6, m), 0.8 (3, t)
Purity:>95%

10-(9(10)-hydroxy-10(9)-(propionyloxy)octadecanoyloxy)decane-1,2diyl dipropionate (F3)

Pure compound F3 was given as colorless oil by column chromatography with Ethyl acetate/Hexane=1:6.
Yield: 19.8% F3+64.3% F2-M at 95° C., 51.3% F4+30% F3 at 120° C.
1H-NMR in CDCl$_3$ (ppm), 5.1 (1, m), 4.8 (1, m), 4.2 (1, d), 4.0 (3, m), 3.7 (3, br), 2.3 (8, m), 1.6 (8, m), 1.5-1.2 (33, m), 1.1 (9, m), 0.8 (3, t)
MS (+Na$^+$), 679.3
Purity:>95%

1-(9,10-bis(propionyloxy)decyloxy)-1-oxooctadecane-9,10diyl dipropionate (F4)

Pure compound F4 was given as colorless oil by column chromatography with Ethyl acetate/Hexane=1:6.
Yield: 51.3% F4+30% F3 at 120° C.
1H-NMR in CDCl$_3$ (ppm), 5.1 (1, m), 5.0 (2, m), 4.2 (1, d), 4.0 (3, m), 2.3 (10, m), 1.7-1.4 (10, m), 1.4-1.2 (30, m), 1.1 (12, m), 0.8 (3, t)
MS (+Na$^+$)735.6
Purity:>95%

Branched Derivatives of Compound G

Branched compound G derivatives were prepared from the epoxide of compound G and propionic acid at 95° C. for G2 and G3 or 120° C. for G3 and G4 (shown in FIG. 12).

9-hydroxy-10-(propionyloxy)decyl 9-hydroxy-10-(propionyloxy)decanoate (G2-1)

Pure compound G2-1 was given as white solid by column chromatography with Ethyl acetate/Hexane=1:2.
Yield: 47.7% G3+51.2% G2-M at 95° C.
1H-NMR in CDCl$_3$ (ppm), 4.9 (1, br), 4.2 (2, d), 4.0 (2, m), 3.9 (2, dd), 3.8 (2, br), 3.7-3.6 (1, m), 2.4 (4, m), 2.2 (2, t), 1.6 (5, m), 1.5 (4, m), 1.4-1.2 (17, m), 1.1 (6, t)
Purity:>95%

10-hydroxy-9-(propionyloxy)decyl 9-hydroxy-10-(propionyloxy)decanoate or/and 9-hydroxy-10-(propionyloxy)decyl 10-hydroxy-9-(propionyloxy)decanoate (G2-2)

Pure compound G2-2 was given as white solid by column chromatography with Ethyl acetate/Hexane=1:2.
Yield: 47.7% G3+51.2% G2-M at 95° C.
1H-NMR in CDCl$_3$ (ppm), 4.9 (1, br), 4.2 (2, d), 4.0 (2, m), 3.9 (2, dd), 3.8 (2, br), 3.7-3.6 (1, m), 2.4 (4, m), 2.2 (2, t), 1.6 (5, m), 1.5 (4, m), 1.4-1.2 (17, m), 1.1 (6, t)
MS (+Na$^+$):511.3
Purity:>95%

10-(9-hydroxy-10-(propionyloxy)decanoyloxy)decane-1,2diyl dipropionate or/and 10-(9-hydroxy-10-(propionyloxy)decyloxy)-10-oxodecane-1,2diyl dipropionate (G3-1)

Pure compound G3-1 was given as colorless oil by column chromatography with Ethyl acetate/Hexane=1:3.
Yield: 47.7% G3+51.2% G2-M at 95° C., 57.2% G4+21.5% G3 at 120° C.
1H-NMR in CDCl$_3$ (ppm), 5.1 (1, br), 4.2 (1, d), 4.1 (1, d), 4.0 (2, m), 3.9 (2, dd), 3.8 (1, br), 2.3 (8, m), 1.7-1.2 (27,m), 1.1 (9, m)
Purity:>95%

10-(10-hydroxy-9-(propionyloxy)decanoyloxy)decane-1,2diyl dipropionate or/and 10-(10-hydroxy-9-(propionyloxy)decyloxy)-10-oxodecane-1,2diyl dipropionate (G3-2)

Pure compound G3-2 was given as colorless oil by column chromatography with Ethyl acetate/Hexane=1:3.
Yield: 0.47.7% G3+51.2% G2-M at 95° C., 57.2% G4+21.5% G3 at 120° C.
1H-NMR in CDCl$_3$ (ppm), 5.1 (1, br), 4.2 (1, d), 4.1 (1, d), 4.0 (2, m), 3.9 (2, dd), 3.8 (1, br), 2.3 (8, m), 1.7-1.2 (27,m), 1.1 (9, m)
Purity:>95%

10-(9,10-bis(propionyloxy)decanoyloxy)decane-1,2diyl dipropionate (G4)

Pure compound G4 was given as colorless oil by column chromatography with Ethyl acetate/Hexane=1:5.
Yield: 57.2% G4+21.5% G3 at 120° C.
1H-NMR in CDCl$_3$ (ppm), 5.1 (2, m), 4.2 (2, d), 4.0 (4, m), 2.3 (10, m), 1.6 (7, m), 1.5 (18, m) 1.1 (12, m)
Purity:>95%

Synthesis of (E)-didec-9-enyl octadec-9-enedioate and its branched compounds (Compound H)

Materials:
Oleic acid (90%), Grubbs metathesis catalyst (2$^{nd}$ generation catalyst), 9-decen-1-ol, Propionic acid, Chloroform, Dichloromethane, N,N'-Dicyclohexylcarbodiimide (DCC), 4-Dimethylaminopyridine (DMAP), Formic acid, hydrogen peroxide were purchased from Sigma-Aldrich. Hexane and Ethyl Acetate from ACP Chemical Int. (Montreal, Quebec, Canada) were used without further treatment. The synthesis procedure for compound H is shown in FIG. 13.
E-didec-9-enyl octadec-9-enedioate was prepared from 9-decen-1-ol and 1,18-Octadec-9-enedioic acid which was prepared from Oleic acid by metathesis reaction with Grubbs catalyst (2$^{nd}$ generation).

Synthesis of 1,18-Octadec-9-enedioic acid

Oleic acid (76 g (270 mmol)) was transferred into a 250 ml three-necked round bottomed flask and stirred at a temperature typically between 10-100° C., preferably between about 30-70° C., and most preferably at 45° C. under nitrogen gas for 0.5 h. Grubbs metathesis catalyst 2$^{nd}$ generation (85 mg) was added. The reaction mixture was stirred at 45° C. for around 5 min, at which point diacid (1,18-Octadec-9-enedioic acid) began to be precipitated from the reaction mixture.

The reaction was kept at this temperature for 24 hours and then it was quenched with ethyl vinyl ether (15 ml), and excess ether was removed under reduced pressure. The residue was purified by recrystallization from ethyl acetate and hexane (1:2) to give 29.75 g of product as a white solid.

Yield: 72%

1H-NMR in DMSO-d6 (ppm): 12 (2H, s, —COOH), 5.3 (2H, t, —CH=CH—), 2.2 (4H, m, —CH2-COOH), 1.9 (4H, m, —CH2-CH=), 1.4 (4H, m, —CH2-$\overline{\text{CH}}$2-COOH), 1.3-1.2 (18H, $\overline{\text{m}}$, CH2)

Purity: >95%

Synthesis of (E)-didec-9-enyl octadec-9-enedioate (H)

To the solution of 1,18-Octadec-9-enedioic acid (15.6 g, 50 mmol) and 9-decen-1-ol (23.4 g, 150 mmol) in CHCl$_3$ at around 0° C., DMAP(12.2 g, 100 mmol) was added, followed by slow addition of DCC (22.7 g, 110 mmol). The reaction mixture was allowed to be warmed to room temperature and kept overnight. The mixture was filtered to remove solid. The filtrate was concentrated on a rotary evaporator. The residue was purified by flash chromatography using Ethyl acetate/Hexane (1:40) to give 28 g of product as a colorless oil.

1H-NMR in CDCl$_3$ (ppm): 5.8 (2H, m, =CH—), 5.4 (2H, t, —CH=CH—), 5.0-4.8 (4H, dd, CH2=), 4.0 (4, t, —CH2-O), 2.3 (4H, t, O=C—CH2-), 2.1-1.8 (8H, m, =CH—C$\overline{\text{H}}$2-), 1.6 (8H, m, —CH2-CH2-O—), 1.4-1.2 (36, m, $\overline{\text{—}}$CH2-)

Purity: >95%

Epoxidation of H (FIG. 14)

To a stirred solution of ester (2.7 g, 4.56 mmol) and formic acid (2.2 g, 9 mmol) in 3 mL CH$_2$Cl$_2$ at 4° C., H$_2$O$_2$ (30%) (3.4 g, 6.6 mmol) was slowly added. The reaction proceeded at room temperature with vigorous stirring for 48 hrs. After removal of the water phase, more CH$_2$Cl$_2$ (10 mL) was added to organic phase, which was washed sequentially with water (2×20 mL) sat. aq NaHCO$_3$ (2×10 mL) and brine (2×20 mL), dried on Na$_2$SO$_4$, filtered, and concentrated on a rotary evaporator. The residue was purified by column chromatography with Ethyl acetate/Hexane=1:4 to give 2.1 g of white solid.

Yield: 72%

1H-NMR in CDCl$_3$ (ppm): 4.0 (4H, t, —CH2-O—), 2.9 (2H, m), 2.7 (2H, t), 2.6 (2H, t), 2.4 (2H, dd), 2.3 (4H, t, O=C—CH2-), 1.7-1.2 (52H, m)

Purity: >95%

Synthesis of Branched compounds of Compound H (FIG. 14)

The branched compounds below are referred to as H3 (3-branched), H4 (4-branched), H5 (5-branched), and H6 (6-branched). To the epoxidation products above (1.6 g, 4.7 mmol), 15.47 mmol propionic acid was added. The reaction was carried out under an N$_2$ atmosphere and heated to typically between 50-150° C., preferably between about 70-120° C., and most preferably at 95° C. and stirred at 95° C. for typically between about 4 to 36 hours, preferably 10-20 hours, and most preferably 16 hours. To achieve 5 or 6 branches in the compounds, the reaction temperature was raised to typically between 60-160° C., preferably between about 80-140° C., and most preferably at 120° C. The resulting products were poured into 10 ml of water and extracted with Ethyl acetate (2×10 mL). The organic phase was washed sequentially by water (2×10 mL), sat. aq NaHCO$_3$ (2×10 mL) and brine (2×20 mL), dried on Na$_2$SO$_4$, then filtered and concentrated on a rotary evaporator. The residue was purified by column chromatography with Ethyl Acetate/Hexane (1:1 for H3, 1:2 for H4, 1:3 for H5 and 1:4 for H6).

Yield: 37.5% H3+43.8% H4+11.5% H5 at 95° C., and 43.7% H5+38.4% H6 at 120° C.

1H-NMR in CDCl$_3$ (ppm)

1-(9(10)-hydroxy-10(9)-(propionyloxy)decyl) 18-(10(9)-hydroxy-9(10)-(propionyloxy)decyl)-9(10)-hydroxy-10(9)-(propionyloxy)octadecanedioate (H3)

5.1-4.8 (2H, m), 4.3-4.1 (2H, dd), 4.0 (4H, t), 4.0-3.9 (2H, dd), 3.8 (1H, m), 3.7-3.5 (2H, m), 2.4-2.2 (10H, m), 1.9 (3H, br, —OH), 1.6-1.2 (52H, m), 1.2-1.0 (9H, t, —CH3).

MS (M+Na$^+$): 881.5

Purity: >95%

1-(9,10-bis(propionyloxy)decyl) 18-(9(10)-hydroxy-10 (9)-(propionyloxy)decyl) 10(9)-hydroxy-9(10)-(propionyloxy)octadecanedioate (H4)

5.2-4.8 (3H, m), 4.3-4.1 (2H, dd), 4.0 (4H, m), 4.0-3.9 (1, dd), 3.8 (1H, m), 3.7-3.5 (2H, m), 2.4-2.2 (12H, m), 1.9 (2H, br, —OH), 1.7-1.2 (52H, m), 1.1 (12H, m, —CH3).

MS (M+Na$^+$): 937.6

Purity: >95%

Bis(9,10-bis(propionyloxy)decyl)9(10)-hydroxy-10(9)-(propionyloxy)octadecandioate (H5): 5.2-4.7 (3H, m), 4.2 (2H, dd), 4.0 (6H, m), 3.6 (1H, m), 2.3 (14H, m), 1.6-1.4 (16, m), 1.4-1.2 (36H, m), 1.1 (15, m)

MS (M+Na$^+$): 993.9

Purity:>95%

Bis(9,10-bis(propionyloxy)decyl)9,10-bis(propionyloxy) octadecanedioate (H6): 5.1 (2H, m), 4.9 (2H, m), 4.2 (2, dd), 4.0 (6H, q), 2.3 (16H, m), 1.7-1.4 (16H, m), 1.4-1.2 (36H, m), 1.1 (18, m)

MS (M+Na$^+$): 1049.9

Purity:>95%

Composition of Crude Samples

Several compounds described herein are crude samples, as in they are mixtures of existing branched derivatives of a dimer and/or trimer ester. Compounds E95, F95, G95, and H95 are the crude samples of compounds E F, G, and H, respectively. These are mixtures of branched compounds of compounds E F, G, and H, respectively, which were prepared from their epoxides and propionic acid at 95° C. Reaction time for these compounds was 24 hours. Similarly, compounds E120, F120, and G120 are crudes of compounds E, F, and G, respectively, prepared at 120° C. for 24 hours. H120A is the crude sample of compound H prepared at 120° C. for 16 hours. H120 B is the crude sample of compound H prepared at 120° C. for 26 hours. As referred to at a later point in this application, H120C is the crude sample of compound H prepared at 120° C. for 26 hours, and H120-20H is the crude sample of compound H prepared at 120° C. for 20 hours. The Table 4 below summarizes the specific compositions of the above crude samples. Also in Table 4 below, "NI" means "not identified."

TABLE 4

Compositions of H branched compounds (%)

| Name | H3 | H4 | H5 | H6 | NI | water |
|---|---|---|---|---|---|---|
| H95 (26 hours) | 37.48 | 43.83 | 11.69 | 0 | 7 | — |
| H120A (16 hours) | 6.31 | 39.66 | 35.82 | 6.14 | 3.72 | 8 |
| H120B (26 Hours) | 0 | 7.12 | 33.7 | 38.43 | 20.75 | — |
| 120A Dry | 7.23 | 43.11 | 38.94 | 6.67 | 4.05 | — |

TABLE 4-continued

Compositions of E branched compounds

| Name | E2 | E3 | E4 | NI | — | — |
|---|---|---|---|---|---|---|
| E95 | 88.06 | 11.39 | — | — | — | — |
| E120 | 6.46 | 77.83 | 15.7 | — | — | — |

Compositions of G branched compounds

| Name | G2 | G3 | G4 | NI | — | — |
|---|---|---|---|---|---|---|
| G95 | 30.66 | 56.97 | 12 | — | — | — |
| G120 | 3.5 | 44.52 | 51.08 | — | — | — |

Compositions of F branched compounds

| Name | F2 | F3 | F4 | NI | — | — |
|---|---|---|---|---|---|---|
| F95 | 85.43 | 12.82 | — | 1.75 | — | — |
| F120 | 39.12 | 53.01 | 4.28 | 3.60 | — | — |

Study of Time and Temperature Dependence of the Ring-opening Reaction of Epoxides by Propionic Acid Exhaustive efforts were made to synthesize pure samples of the base esters A-H and their individual branched derivatives, so as to understand the influence of structure on lubrication and low temperature fluidity properties. In this section, the mixture of branched products arising out of the epoxide of certain base esters (compounds E, G, and H), was studied by controlling the temperature of the ring-opening reaction and quenching the reaction at various time periods (as generically shown in FIG. 15).

By managing the degree of ring opening, the structure of the complex ester mixture is altered so that the low temperature properties of the fluids are adjusted to best fit various applications. Due to their asymmetric structures and terminal epoxide rings, the ring-opening esterification of compounds E, G, and H derivatives are complex. In order to optimize the reaction conditions and better control the ring-opening esterification, so as to produce an optimized mixture of structures in the complex ester mixture which then delivers unique functionality for specific applications, it is important to understand the time-temperature dependence of the reaction.

Materials:

Compounds E, G, and H were prepared from Oleic acid, 9-decenoic acid and 9-decen-1-ol as detailed above; Propionic acid, $H_2O_2$, and Formic acid were purchased from Sigma-Aldrich. FIGS. 16-18 show the reactions that were being performed, to varying degrees, for compounds E, G, and H.

Method:

The epoxides were prepared from esters of E, G, and H, followed by ring-opening reactions with propionic acid using solvent-free conditions, as described above. The reactions were carried out at 95° C. and 120° C. for 24 hours and at 140° C. for 8 hours. HPLC-ELSD was used to monitor the ring-opening reactions.

The samples were measured on Waters e2695 HPLC with Waters 2424 ELS Detector and C18 column (5 um 4.6×150 mm). The mobile phase was mixture of 85% ACN: 15% water with a flow rate of 1 mL/min. The individual pure branched derivatives were first used as standards, so that the complex mixtures could be analyzed with confidence.

The following Tables 5 through 13 show the evolution of the various branched species of several base esters with time at the various temperatures. These complex mixtures were also analyzed for lubricating and low temperature fluidity and the structure-function relationships examined, separately below.

Tables 5 through 13: Time-Temperature dependence of ring opening reactions

TABLE 5

Composites of ring-opening of epoxide of G at 95° C.

| Time (hours) | G2 | G3 | G4 | SM | G1R |
|---|---|---|---|---|---|
| 0.00 | | | | 100.00 | |
| 1.00 | 3.14 | 0.00 | 0.00 | 58.63 | 38.23 |
| 2.00 | 20.25 | 0.00 | 0.00 | 21.51 | 58.23 |
| 4.00 | 64.71 | 5.57 | 0.00 | 5.57 | 29.70 |
| 6.00 | 81.26 | 8.08 | 0.00 | 0.00 | 10.66 |
| 8.00 | 79.35 | 16.73 | 0.00 | | 3.64 |
| 11.00 | 69.94 | 27.82 | 1.23 | | 0.67 |
| 13.00 | 61.69 | 35.52 | 2.13 | | 0.26 |
| 24.00 | 30.66 | 56.97 | 12.00 | | |

TABLE 6

Composites of ring-opening of epoxide of G at 120° C.

| Time (hours) | G2 | G3 | G4 | SM | G1R |
|---|---|---|---|---|---|
| 0.00 | | | | 100.00 | |
| 1.00 | 27.63 | 16.96 | 0.00 | 16.91 | 54.97 |
| 2.00 | 73.54 | 18.63 | 0.00 | 7.25 | 18.63 |
| 4.00 | 66.16 | 31.58 | 1.85 | | 0.41 |
| 6.00 | 44.11 | 48.82 | 7.06 | | |
| 8.00 | 29.00 | 57.26 | 13.66 | | |
| 11.00 | 13.52 | 57.18 | 29.00 | | |
| 24.00 | 0.69 | 21.34 | 76.38 | | |

TABLE 7

Composites of ring-opening of epoxide of G at 140° C.

| Time (hours) | G2 | G3 | G4 | SM | G1R |
|---|---|---|---|---|---|
| 0.00 | | | | 100.00 | |
| 0.50 | 51.92 | | | 6.27 | 41.46 |
| 1.00 | 82.14 | 7.28 | | | 7.28 |
| 2.00 | 68.41 | 29.89 | 1.39 | | 0.17 |
| 3.00 | 45.12 | 49.11 | 5.59 | | |
| 4.00 | 33.01 | 56.70 | 10.13 | | |
| 5.00 | 24.68 | 58.99 | 16.16 | | |
| 6.00 | 14.96 | 58.04 | 26.80 | | |
| 7.00 | 4.73 | 45.94 | 49.13 | | |
| 8.50 | 3.50 | 44.52 | 51.08 | | |

TABLE 8

Composites of ring-opening of epoxide of H at 95° C.

| Time (hours) | H3 | H4 | H5 | H2R | H1R | SM |
|---|---|---|---|---|---|---|
| 0.00 | | | | | | 100.00 |
| 1.00 | | | | 11.30 | | 88.70 |
| 2.00 | 0.26 | | | 40.83 | 6.23 | 52.68 |
| 3.00 | 2.03 | | | 51.13 | 19.07 | 27.77 |
| 5.00 | 11.56 | | | 37.00 | 43.49 | 7.95 |
| 7.00 | 26.25 | 2.76 | | 18.08 | 46.89 | 6.03 |
| 9.00 | 40.93 | 6.69 | | 8.45 | 39.89 | 3.96 |
| 13.00 | 55.18 | 16.31 | | 3.76 | 20.44 | 4.31 |
| 26.00 | 37.48 | 43.84 | 11.48 | 3.28 | 7.90 | 2.26 |

TABLE 9

Composites of ring-opening of epoxide of H at 120° C.

| Time (hours) | H3 | H4 | H5 | H6 | H2R | H1R | SM |
|---|---|---|---|---|---|---|---|
| 0.00 | | | | | | | 100.00 |
| 1.00 | 8.20 | | | | 40.28 | 42.74 | 8.78 |
| 2.00 | 40.06 | 4.88 | | | 42.29 | 8.69 | 4.08 |
| 3.00 | 59.50 | 14.43 | | | 18.51 | 2.64 | 4.29 |
| 5.00 | 50.58 | 36.29 | 5.23 | | 3.19 | 2.22 | 2.48 |
| 7.00 | 30.80 | 49.95 | 14.95 | 0.96 | 2.19 | | 1.14 |
| 9.00 | 20.83 | 50.30 | 23.62 | 2.54 | 2.72 | | |
| 12.00 | 9.16 | 41.74 | 37.44 | 6.13 | | | |
| 24.00 | | 9.46 | 46.53 | 33.65 | | | |
| 26.00 | | 7.12 | 43.70 | 38.43 | | | |

TABLE 10

Composites of ring-opening of epoxide of H at 140° C.

| Time (hours) | H3 | H4 | H5 | H6 | H1R | H2R | SM |
|---|---|---|---|---|---|---|---|
| 0.00 | | | | | | | 100.00 |
| 0.50 | 2.86 | | | | 36.22 | 54.11 | 6.82 |
| 1.00 | 61.51 | | | | 38.49 | | |
| 1.50 | 81.74 | 9.70 | | | 8.56 | | |
| 2.00 | 73.78 | 23.71 | | | 2.51 | | |
| 3.00 | 59.59 | 40.41 | | | | | |
| 4.00 | 37.82 | 59.91 | 2.26 | | | | |
| 5.00 | 25.59 | 66.87 | 6.48 | | | | |
| 6.00 | 20.81 | 70.13 | 9.06 | | | | |
| 7.00 | 15.70 | 68.76 | 14.11 | 0.91 | | | |
| 8.00 | 10.20 | 67.08 | 19.66 | 1.89 | | | |
| 24.00 | | | 12.09 | 52.74 | | | |

TABLE 11

Composites of ring-opening of epoxide of E at 95° C.

| Time (hours) | E2 | E3 | E4 | E1R1 | E1R1 | SM |
|---|---|---|---|---|---|---|
| 0.00 | | | | | | 100.00 |
| 1.00 | 1.09 | | | 18.09 | 5.00 | 75.70 |
| 2.00 | 13.71 | | | 44.17 | 11.09 | 31.03 |
| 4.00 | 57.75 | | | 33.68 | 6.22 | 2.34 |
| 6.00 | 81.04 | | | 17.34 | 1.62 | |
| 8.00 | 91.64 | 1.53 | | 6.83 | | |
| 10.00 | 95.15 | 2.44 | | 2.42 | | |
| 12.00 | 95.27 | 4.73 | | | | |
| 24.00 | 88.06 | 11.39 | | | | |

TABLE 12

Composites of ring-opening of epoxide of E at 120° C.

| | E2 | E3 | E4 | E1R1 | E1R2 | SM |
|---|---|---|---|---|---|---|
| 0.00 | | | | | | 100.00 |
| 0.50 | 13.12 | | | 43.04 | 9.82 | 34.02 |
| 1.00 | 68.50 | | | 27.85 | 3.65 | |
| 2.00 | 95.91 | | | 4.20 | | |
| 3.00 | 97.52 | 2.48 | | | | |
| 4.00 | 94.21 | 5.79 | | | | |
| 6.00 | 87.99 | 12.00 | | | | |
| 8.00 | 69.72 | 30.28 | | | | |
| 10.00 | 59.35 | 40.65 | | | | |
| 12.00 | 44.31 | 55.02 | 0.67 | | | |
| 24.00 | 6.46 | 77.83 | 15.70 | | | |

TABLE 13

Composites of ring-opening of epoxide of E at 140° C.

| Time (hours) | E2 | E3 | E4 | E1R1 | E1R2 | SM |
|---|---|---|---|---|---|---|
| 0.00 | | | | | | 100.00 |
| 0.50 | 82.47 | | | 19.54 | | 0.00 |
| 1.00 | 100.00 | | | | | |
| 1.50 | 96.45 | 3.55 | | | | |
| 2.00 | 91.43 | 8.57 | | | | |
| 3.00 | 74.33 | 25.66 | | | | |
| 4.00 | 61.90 | 48.10 | | | | |
| 6.00 | 20.70 | 74.80 | 4.50 | | | |
| 7.50 | 9.63 | 81.50 | 8.87 | | | |

II. Experimental Methods—Measurement of Physical Properties

For the synthesized dimer esters and trimer esters (compounds A-H), and their respective branched derivatives described above, the following describes the experimental methods utilized to measure physical properties of the aforesaid compounds.

Differential Scanning Calorimetry

The cooling and heating profiles of all compounds were carried out using a Q200 model DSC (TA Instruments, DE, USA) equipped with a refrigerated cooling system (RCS 90, TA Instrument).

Approximately 5.0-10.0 (±0.1) mg of fully melted and homogenously mixed sample was placed in an aluminum DSC pan which was then hermetically sealed. An empty aluminum pan was used as a reference and the measurements were performed under a nitrogen flow of 50 mL/min.

The "TA Universal Analysis" software coupled with a published method (Use of first and second derivatives to accurately determine key parameters of DSC thermographs in lipid crystallization studies. Thermochimica Acta, 2005. 439 (1-2): p. 94-102, Bouzidi et al., 2005) was used to analyze the data and extract the main characteristics of the peaks (temperature at maximum heat flow, $T_m$; onset temperature, $T_{on}$; offset temperature, $T_{off}$; enthalpy, $\Delta H$; and full width at half maximum, FWHM). The temperature window over which a thermal event occurs is defined as the absolute value of the difference between $T_{off}$ and $T_{on}$ of that event. It is labeled $\Delta T_C$ for crystallization and $\Delta T_M$ for melting. The characteristics of the shoulders when present were estimated using a simple decomposition of the signal into its obvious main components. The positions in this case were estimated using the first and second derivatives of the differential heat flow.

The samples were subjected to cooling profiles which allow for comparison between the different techniques used. The samples were heated to 50° C. and held for 5 min, a temperature and a time over which crystal memory is erased, and then cooled at a constant rate of 3.0° C./min, to a finish temperature of −90° C., where it was held isothermally for a 5 min. The sample was then reheated at a constant rate of 3.0° C./min to 70° C. to obtain the melting profile.

In some instances (E2-2, E2-M, F2-1, F2-2, F3, F4), a 0.1° C./min cooling rate was used. The sample in this case was heated to 90° C. and held for 5 min and then cooled at the constant rate down to −90° C. where the sample was held isothermally for 5 min then reheated to 90° C. at a constant rate of 3.0° C./min to obtain the heating profile.

Thermo Gravimetric Analysis

The TGA measurements were carried out on a TGA Q500 (TA Instruments, DE, USA) equipped with a TGA heat exchanger (P/N 953160.901). Approximately 8.0-15.0 mg of fully melted and homogenously mixed sample was loaded in the open TGA platinum pan. The sample was heated from 25 to 600° C. under dry nitrogen at a constant heating rate of 3° C./min. The TGA measurements were performed under a nitrogen flow of 40 mL/min for balance purge flow and 60 mL/min for sample purge flow. All the samples were run in triplicate.

The samples which were run by TGA are: A, B, C, D, A2, C2, E2 G4, H5, H6, E, F, G, E95, E120, F95, F120, G95, G120, G140, H95, H120A, and H120B.

Viscosity Measurement

Sample viscosities were measured on a computer-controlled rheometer, AR2000ex, equipped with a standard AR Series Peltier Plate and Peltier AR series Concentric Cylinder (TA Instruments, DE, USA). The circulating fluid heat exchange medium was provided either by a TA heat exchanger (TA P/N 953/160.901) or a temperature controlled circulating water bath (Julabo F25, Allentown, Pa.). The AR Series Peltier Plate has a 80-mm diameter hardened chrome surface and can provide a continuous temperature range of −20° C. to 180° C. when used with circulating water at 1° C. and −40° C. to 160° C. when an appropriate circulating fluid at −20° C. is used. The AR Series Peltier concentric cylinder can provide a continuous temperature range of 0° C. to 100° C. when used with circulating water at 1° C. and −40° C. to 100° C. when an appropriate circulating fluid at −20° C. is used. The internal resolution of both systems is 0.01° C. The AR Series plate and cylinder offer typical heating rates of up to 50 and 13° C./min, respectively and a temperature accuracy of 0.1° C.

The experiments were performed under an air bearing pressure at 27 psi. A 40-mm 2° steel cone (SIN 511406.901) geometry was used for testing high viscosity materials and a standard-size recessed-end concentric cylinder (stator inner radius 15 mm and rotor outer radius 14 mm, SIN 545023.001) for low viscosity materials. Approximately 0.59 mL and 6.65 mL of fully melted and homogenously mixed sample was used in the parallel plate and concentric cylinder geometry, respectively. Circulating water at 0° C. in the TA heat exchanger and 6° C. in the circulating bath were used and temperatures as low as −10° C. and as high as 120° C. were easily obtained with an accuracy of 0.1° C.

Viscosities of samples were measured from temperatures above each sample's melting point up to 110° C. The measurements were performed using 3 methods: 1. Shear rate/ share stress curves, 2. Constant Temperature Rate, Constant shear rate procedure, and 3. Peak hold procedure. The viscosities measured viscosities were found in good agreement within experimental uncertainty.

Shear rate/share stress curves (increasing and decreasing shear rate)

The procedure was carried out by controlling shear rate, and measurements were performed in 10° C. steps. The shear rate range was optimized for torque (lowest possible is 10 μNm) and velocity (maximum supplier suggested of 40 rad/s). At each measurement temperature, the lowest shear rate accessible was determined by controlling the lowest torque available compatible with the temperature, and the highest shear rate was determined by increasing the applied torque to a level where the maximum suggested velocity is reached. Typical optimization results are summarized in Table 14 below.

TABLE 14

Typical optimized shear rate limits for different temperatures of measurements.

| Temperature (° C.) | shear rate (s$^{-1}$) | |
|---|---|---|
| | Lower limit | Upper limit |
| 110 | 100 | 1200 |
| 100 | 50 | 1200 |
| 90 | 10 | 1200 |
| 80 | 10 | 1200 |
| 70 | 10 | 1200 |
| 60 | 1 | 1200 |
| 50 | 1 | 1200 |
| 40 | 1 | 1200 |
| 30 | 0.5 | 1200 |
| 20 | 0.1 | 1200 |
| 10 | 0.1 | 700 |
| 0 | 0.01 | 700 |
| −10 | 0.01 | 500 |

We have used three (3) available shear rate/share stress procedures to determine viscosity:

Continuous Ramp Procedure:

The sample was first heated to 110° C. and equilibrated for 5 min and a continuous ramp procedure was initiated from 110° C. down to the melting temperature by 10° C. steps. The procedure is repeated for each temperature with 5 min equilibration time at each temperature. Shear rate was increased from lower to upper shear rate according to Table 14. Duration was 10 min in the log mode and sampling was 20 point per decade. G4 was also run with decreasing shear rate to allow for comparison.

Steady State Flow Procedure:

This procedure was used for a limited number of samples (which are E2-2, E95, E120, F95, F120, G95, G120, H95, H120A, H120A_dry, H120B, H3, H4, H5 and H6) for comparison and optimization purposes. The sample was also heated to 110° C. and equilibrated for 5 min and the continuous ramp procedure was initiated down to the melting temperature by 5° C. steps. The procedure is repeated for each temperature with 5 min equilibration time at each temperature. Increasing shear rate from the lower limit to the upper limit was used in the linear mode with 25 s$^{-1}$ steps and sampling period of 1 min.

Step Flow Procedure

The step flow procedure was only used for one sample (G3-1). The sample was first measured at its melting point (0° C.) then at increasing temperatures (10° C. steps). The sample was equilibrated for 5 min at the measurement temperature and then subjected to the step flow procedure using 20 sampling points per decade, a constant time of 30 s, and average last 10 seconds. Shear rate was increased from its lower to its upper limit according to Table 14.

Constant Temperature Rate Procedure

In order to speed up data collection, cooling and heating rate procedures were tested and compared to the shear rate/ shear stress procedure. The sample was quickly heated to 110° C. and equilibrated at this temperature for 5 min then cooled down at a constant rate (3.0° C./min) to its melting temperature. A constant shear rate of 200 s$^{-1}$ was chosen as it was the lowest common shear rate which yielded a constant viscosity in the range applied (Newtonian behavior-characterized by having a shear stress that is linearly proportional to the shear strain rate) as determined from the continuous ramp procedure. Sampling points were recorded every 1° C. All other measurement conditions were kept constant.

Some samples (E2-2, F2-2, G3-1, H120B) were run using decreasing temperature ramp at the same conditions. Other samples (E2-2, G3-1, E95, E120, F120, G95, G120, H95, H120A, H120A_dry, H120B, H3, H4, H5 and H6) were run at decreasing temperature using a rate of 1.0° C./min. G3-1 was also run at increasing temperature using a rate of 1.0° C./min.

Peak Hold Procedure

The peak hold procedure is an alternative to the constant rate procedure. It also uses a fixed shear rate and is based on the equilibration and holding of the sample at a set temperature, measurement of viscosity and subsequent stepping the temperature for another equilibration, holding and measurement. This procedure was used only for one sample (G3-1) and was found comparable and therefore was not employed further. The procedure was started at the sample melting point (−1° C.) and 3 C steps with 5 min equilibration and 10 min duration time. A shear rate of 200 s$^{-1}$ was used.

III. Properties of the Compounds of this Invention

The dimer and trimer esters and their branched derivatives of the present invention exhibit improved viscosity at the full range of operating conditions, improved oxidative stability (meaning removal of double bonds in the case of natural oil derived materials), and improved thermal stability. In particular, we have discovered that in the branched derivatives, branching the hydrocarbon backbone in an asymmetrical fashion greatly improves low temperature performance, and has improved fluidity at low temperatures in an unexpected manner. These aspects are described in further detail below.

Table 15 below shows the crystallization onsets, onsets and offsets of melt (all in ° C.), and dynamic viscosities at 0° C., 20° C., 40° C., and 100° C. (in m-Pascal-seconds, or mPa·s), of all the compounds created in this invention.

TABLE 15

Crystallization onsets, onsets and offsets of melt (all in ° C.), and dynamic viscosities at 0° C., 20° C., 40° C., and 100° C. (in mPa · s), of all the compounds created in this invention.

| Sample | Crystallization Onset (° C.) | STD | Melting Onset (° C.) | STD | Final Melting Offset (° C.) | STD | Viscosity at 0° C. | Viscosity at 20° C. | Viscosity at 40° C. | Viscosity at 100° C. |
|---|---|---|---|---|---|---|---|---|---|---|
| A | −0.69 | 0.26 | −12.29 | 0.05 | 10.01 | 0.07 | 90 | 29.8 | 16.0 | 5.2 |
| A2 | −37.67 | 1.02 | −57.81 | 0.36 | −40.27 | 0.16 | 12210 | 1706.0 | 391.1 | 27.5 |
| A2-II | −27.40 | 0.35 | −20.32 | 0.32 | 29.18 | 0.34 | N/A | N/A | N/A | N/A |
| A3 | −48.70 | 1.09 | −68.57 | 0.04 | −53.55 | 0.51 | 3850 | 712.0 | 199.5 | 20.8 |
| A4 | −55.00 | 5.44 | −72.71 | 0.40 | −61.99 | 0.10 | 1876 | 407.4 | 129.9 | 17.0 |
| B | 15.20 | 1.57 | 0.58 | 0.09 | 16.84 | 0.84 | Not Liquid | 40.7 | 20.9 | 5.9 |
| B2 | −34.66 | 0.07 | −32.87 | 0.03 | 50.36 | 1.24 | 13000 | 1846.0 | 426.0 | 29.8 |
| B3 | −43.02 | 0.05 | −57.54 | 0.28 | −34.74 | 0.55 | 3970 | 710.9 | 236.3 | 23.3 |
| B4 | −50.90 | 3.50 | −72.14 | 0.04 | −39.58 | 1.22 | 2192 | 479.3 | 152.1 | 19.9 |
| C | 25.97 | 0.93 | 14.84 | 0.40 | 30.42 | 0.74 | Not Liquid | Not Liquid | 28.0 | 7.5 |
| C2 | −14.79 | 0.10 | −12.01 | 0.15 | 51.99 | 0.05 | 15030 | 2156.0 | 500.8 | 33.5 |
| C2-II | −5.03 | 0.59 | −4.35 | 0.59 | 3.88 | 0.15 | N/A | N/A | N/A | N/A |
| C3 | −36.10 | 0.36 | −35.37 | 0.83 | −4.99 | 0.23 | 3912 | 78.0 | 227.2 | 24.3 |
| C4 | −50.00 | 0.80 | −70.43 | 0.07 | −12.49 | 0.15 | 2512 | 559.8 | 177.9 | 29.5 |
| D | 14.41 | 3.01 | 2.77 | 0.15 | 23.55 | 2.35 | Not Liquid | 40.3 | 21.0 | 5.9 |
| D2 | −37.90 | 0.04 | −41.15 | 0.04 | −28.21 | 0.32 | 13860 | 1959.0 | 451.5 | 30.7 |
| D3 | −51.50 | 0.50 | −66.38 | 2.15 | −39.37 | 1.49 | 4092 | 777.6 | 221.8 | 22.8 |
| D4 | −50.10 | 5.00 | −71.17 | 0.04 | −61.42 | 0.00 | 2330 | 507.3 | 160.3 | 19.8 |
| E | −13.35 | 0.14 | −13.61 | 0.21 | −6.47 | 0.08 | Not Liquid | 7.5 | 4.8 | 2.2 |
| E2-1 | −25.56 | 4.05 | −67.54 | 0.06 | 27.48 | 0.22 | 4648 | 824.6 | 221.0 | 26.8 |
| E2-2 | −36.14 | 0.73 | −62.39 | 0.20 | −51.23 | 0.55 | 7414 | 1175.0 | 289.7 | 23.2 |
| E2-M | −42.26 | 1.32 | −62.86 | 0.16 | −25.67 | 0.04 | 7279 | 1188 | 300.6 | 28.6 |
| E3 | −50.83 | 1.83 | −75.23 | 0.50 | −60.08 | 0.70 | 2044 | 424 | 130.4 | 16.0 |
| E4 | −36.84 | 25.00 | −76.09 | 0.13 | −68.94 | 0.16 | 1012 | 241.6 | 83.6 | 13.1 |
| F | −5.79 | 0.02 | −19.53 | 0.00 | 5.81 | 0.24 | Not Liquid | 9.049 | 5.7 | 2.3 |
| F2-1 | −14.74 | 0.09 | −67.22 | 0.34 | 41.60 | 0.03 | 5939 | 1010 | 260.2 | 21.8 |
| F2-2 | −40.91 | 1.26 | −61.04 | 0.31 | −50.77 | 0.39 | 5003 | 877 | 232.0 | 29.6 |
| F2-M | −28.58 | 0.47 | −63.05 | 0.48 | 32.90 | 0.30 | 5792 | 984.7 | 255.9 | 22.1 |
| F3 | −56.84 | 1.68 | −77.17 | 1.22 | −61.34 | 0.69 | 2013 | 419.3 | 129.6 | 17.3 |
| F4 | −47.05 | 20.00 | −84.92 | 0.19 | −74.34 | 0.73 | 698 | 179.7 | 66.4 | 11.6 |
| G | −19.47 | 0.77 | −18.30 | 0.11 | −14.70 | 0.28 | Not Liquid | 2.409 | 1.7 | 1.0 |
| G2-1 | 36.76 | 1.79 | −80.35 | 0.54 | 54.66 | 0.02 | Not Liquid | Not Liquid | 170.2 | 19.0 |
| G2-2 | −8.08 | 0.03 | −73.68 | 0.98 | 29.16 | 0.24 | N/A | N/A | N/A | N/A |
| G2-M | 19.28 | 0.20 | −24.48 | 0.71 | 43.41 | 0.17 | Not Liquid | Not Liquid | 183.3 | 21.5 |
| G3-1 | −21.77 | 0.18 | −78.56 | 0.76 | −15.60 | 0.07 | 928 | 224.2 | 78.3 | 11.3 |
| G3-2 | −50.63 | 0.98 | −73.39 | 0.05 | −37.22 | 0.34 | N/A | N/A | N/A | N/A |
| G3-M | −33.85 | 0.21 | −74.73 | 0.20 | −25.46 | 0.21 | 1523 | 341.6 | 113.2 | 16.0 |
| G4 | No crystallization up to −90° C. | | | | | | 379 | 105.8 | 43.4 | 7.9 |
| H | 18.76 | 1.10 | 22.27 | 0.12 | 24.94 | 0.40 | Not Liquid | Not Liquid | 25.4 | 7.1 |
| H3 | −26.71 | 0.10 | −61.49 | 0.13 | 33.96 | 0.64 | 23350 | 3304.0 | 773.0 | 56.1 |
| H4 | −34.73 | 2.94 | −64.37 | 0.12 | 29.66 | 0.50 | 9575 | 1589.0 | 420.1 | 38.9 |
| H5 | −51.78 | 0.36 | −68.10 | 0.21 | 12.35 | 0.35 | 4691 | 891.7 | 260.3 | 28.3 |
| H6 | −49.80 | 0.82 | −71.10 | 0.36 | −20.34 | 1.24 | 3399 | 684.7 | 210.3 | 27.5 |
| E95 | −1.95 | 0.05 | −67.96 | 0.05 | 16.41 | 0.11 | 3363 | 627.9 | 177.9 | 21.0 |
| E120 | −10.02 | 0.07 | −72.74 | 0.16 | −2.29 | 0.81 | 1796 | 385.7 | 121.3 | N/A |
| F95 | −33.83 | 0.16 | −66.35 | 0.06 | 28.32 | 0.34 | Not Liquid | 721.3 | 198.8 | 20.8 |
| F120 | −53.44 | 0.42 | −69.94 | 0.32 | −24.75 | 0.15 | 2751 | 538.2 | 157.7 | 17.2 |
| G95 | −8.73 | 0.47 | −76.68 | 0.41 | 7.97 | 0.43 | 1853 | 408.2 | 133.4 | 18 |
| G120 | −44.38 | 0.34 | −78.41 | 0.01 | −23.71 | 0.37 | 833.1 | 203.7 | 73.2 | 12 |
| H95 | −25.90 | 0.37 | −63.33 | 0.34 | 13.47 | 0.44 | N/A | 2189 | 554.6 | 45.3 |

TABLE 15-continued

Crystallization onsets, onsets and offsets of melt (all in ° C.), and dynamic viscosities at 0° C., 20° C., 40° C., and 100° C. (in mPa · s), of all the compounds created in this invention.

| Sample | Crystallization Onset (° C.) | STD | Melting Onset (° C.) | STD | Final Melting Offset (° C.) | STD | Viscosity at 0° C. | Viscosity at 20° C. | Viscosity at 40° C. | Viscosity at 100° C. |
|---|---|---|---|---|---|---|---|---|---|---|
| H120A | −56.52 | 2.48 | −74.74 | 0.09 | −64.64 | 0.79 | 6999 | 1259 | 346.5 | 36.06 |
| H120A Dry | −43.57 | 2.09 | −66.48 | 0.21 | −58.21 | 0.19 | 7823 | 1371 | 378.4 | 36.7 |
| H120B | −49.71 | 1.97 | −68.11 | 0.05 | −59.75 | 0.09 | 5752 | 1064 | 306.8 | 32.4 |

N/A = Not Available.

Several of the compounds in this invention have superior melt onsets compared to the cited prior art efforts. The onsets of melt, and dynamic viscosities at 40° C. and 100° C. are reported for the cited prior art efforts below in Table 16, for which such information is available. In Table 16, "N/R" means "not reported" for that particular reference.

TABLE 16

Cited prior art properties

| Prior Art | Best Melt Onset (° C.) | Best dynamic viscosity at 40° C. (in m · Pa · s) | Best dynamic viscosity at 100° C. (in m · Pa · s) |
|---|---|---|---|
| Ref. 1 | −20 (pour Point) | N/R | 3 (Kinematic Viscosity in cSt) |
| Ref. 2 | −50 (Melting point) | 16.5 | 3.46 (calculated) |
| Ref. 3 | −37.7 | 8.6 | N/R |
| Ref. 4 | −42 (Pour Point) | N/R | N/R |
| Ref. 5 | −56 | N/R | N/R |
| Ref. 6 | −43 | 679 | 58.6 |
| Ref. 7 | N/R | 400.5 | 43.9 |

In addition, none of the cited prior art documents provide details of the offsets of melt for their respective compounds. The offsets of melt are important because they establish at what temperature the particular compound is completely free of solid material, and is a much more sensitive measurement because of this than pour point or cloud point.

Several of the compounds described in this invention have superior low-temperature fluidity properties, meeting one of the major requirements for natural oil derived lubricants. Low temperature properties are important for lubricant pumpability, filterability, and fluidity as well as cold cranking and startup. Furthermore, the onsets of melt demonstrated by the compounds of this invention are as low as −80° C., besting the cited prior art references in this aspect. Therefore, one improved utility of the compounds of this invention is improved low temperature fluidity or low temperature crystallization.

Table 15 also recites the viscosity at 100° C. of all the compounds described in this invention. If one compares these viscosity measurements with those of the cited prior art, it is clear that the viscosities of the compounds described by this invention span a much larger range, and many are as high as and higher than the highest viscosities of the cited prior art at 100° C. Furthermore, with the range of viscosities at 100° C. of the compounds described in the invention which have onsets of melt equivalent to or less than −40° C., one can see that the range of viscosities at 100° C. which also have superior low temperature fluidity is competitive with the highest recorded viscosities of the cited prior art and offers a much larger viscosity range at this temperature. Furthermore, with the range of viscosities at 40° C. of the compounds described in this invention which have onsets of melt equivalent to or less than −40° C., one can see that the viscosities of compounds in this invention which melt at or below −40° C. are vastly superior to the viscosities of the majority of the compounds of the cited prior art, and such compounds outperform the estolide technology in low temperature fluidity in the cited prior art.

It should also be mentioned that all of the compounds described in this invention are Newtonian (characterized by having a shear stress that is linearly proportional to the shear strain rate) from sub-zero temperatures to 100° C., and that we have been able to develop predictive models which relate the structure of the compounds to their viscosities.

Therefore, another improved utility of these compounds that is claimed is vastly improved viscosity ranges with enhanced low temperature fluidity.

Oxidative Stability

Another important area for improvement of natural oil derived lubricants relate to their oxidative instability due to the presence of carbon-carbon double bonds. It should be noted that all of the branched compounds in this invention are completely devoid of double bonds. They inherently therefore are significantly improved in terms of oxidative stability compared to natural oil derived compounds with remaining double bonds. As commonly understood in the art, oxidative stability defines durability of a lubricant and its ability to maintain functional properties during its use. Therefore, another improved utility that is being claimed is improved oxidative stability.

Thermal Stability

Another important area for improvement for natural oil derived lubricants is in their thermal stability. Thermal Gravimetric Analysis for certain compounds described in this invention (compounds A, B, C, D, E, F, G, A2, C2, E2, G4, H5, H6, H95, H120A, E95, E120, F95, F120, G95, G120 and G140 have been run by TGA) shows that the thermal stability of these compounds were surprisingly high, with these compositions having thermal stability between about 300° C. through about 390° C. Below in Table 17 shows degradation temperatures and associated weight loss values of the compounds run by TGA.

TABLE 17

Degradation temperatures and associated weight loss values of the compounds run by TGA.

| Sample | T1 (° C.) | Loss1 (%) | T2 (° C.) | Loss2 (%) | T3 (° C.) | Loss3 (%) |
|---|---|---|---|---|---|---|
| A | — | — | 317 | 81 | — | — |
| B | — | — | 322 | 84 | — | — |
| C | — | — | 350 | 76 | — | — |
| D | — | — | 329 | 85 | — | — |

TABLE 17-continued

Degradation temperatures and associated weight loss values of the compounds run by TGA.

| Sample | T1 (° C.) | Loss1 (%) | T2 (° C.) | Loss2 (%) | T3 (° C.) | Loss3 (%) |
|---|---|---|---|---|---|---|
| E | — | — | 259 | 81 | — | — |
| F | — | — | 260 | 82 | — | — |
| G | — | — | 197 | 81 | — | — |
| A2 | — | — | 327 | 62 | 414 | 99 |
| C2 | — | — | 391 | 66 | | |
| G4 | — | — | 324 | 63 | 415 | 99 |
| H5 | — | — | 345 | 45 | 423 | 92 |
| H6 | — | — | 343 | 41 | 424 | 93 |
| E95 | — | — | 305 | 58 | — | — |
| E120 | — | — | 309 | 58 | — | — |
| F95 | — | — | 313 | 54 | — | — |
| F120 | — | — | 319 | 56 | — | — |
| G95 | 290 | 46 | 345 | 84 | 415 | 98 |
| G120 | 295 | 10 | 306 | 56 | 415 | 98 |
| G140 | 289 | 53 | 346 | 89 | 413 | 98 |
| H95 | 221 | 2 | 345 | 39 | 423 | 91 |
| H120A | — | — | 350 | 39 | 443 | 87 |
| H120B | 220 | 4 | 342 | 39 | 423 | 90 |

Hydrolytic Stability

Another important area for improvement for natural oil derived lubricants is in their hydrolytic stability. In table 18 below, the tested samples exhibit hydrolytic stability for up to 26 hours:

TABLE 18

| | Hydrolytic Stability | |
|---|---|---|
| Sample | Room Temp. pH[1] | 60° C. for 26 h pH[1] |
| A2 | 3.8 | 3.6 |
| H120 | 3.8 | 3.6 |
| H120C | 3.4 | 3.2 |
| H120-20H | 3.3 | 3.2 |

[1]For the pH tests, 3 g of sample were mixed with 7 g DI H$_2$O in scintillation vials.
The pH of the aqueous layer was then measured with a Mettler Toledo pH probe using a two-point calibration.
The room temperature pH samples were mixed by briefly shaking the vials in hand, while the 60° C. samples were mixed in a shaker.

The foregoing detailed description and accompanying figures have been provided by way of explanation and illustration, and are not intended to limit the scope of the appended claims. Many variations in the present embodiments illustrated herein will be apparent to one of ordinary skill in the art, and remain within the scope of the appended claims and their equivalents.

What is claimed is:

1. A lubricant base stock composition comprising a complex ester having the formula (I):

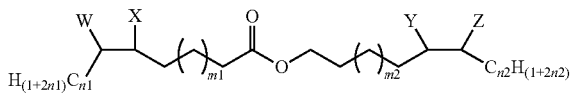

(I)

wherein n1= between 0 and 8; wherein n2= between 0 and 8; wherein m1=between 5 and 9; wherein m2= between 5 and 9; wherein W=OH or OCOR, wherein X=OH or OCOR, with the proviso that when W=OH, then X=OCOR, and when X=OH, then W=OCOR; wherein Y=OCOR or OH; wherein Z=OH or OCOR, with the proviso that when Y=OH, then Z = OCOR, and when Z=OH, then Y=OCOR; and in groups W, X, Y, and Z, R=CiHj, wherein i is 2 or greater and j is 5 or greater.

2. The lubricant base stock composition of claim 1, wherein the composition has a melt onset of between about −5° C. down to about −90° C.

3. The lubricant base stock composition of claim 1, wherein the composition has a dynamic viscosity at 100° C. of between about 7.9 mPascal Seconds and about 33.5 mPascal Seconds.

4. The lubricant base stock composition of claim 1, wherein the composition has a dynamic viscosity at 40° C. of between about 43.4 mPascal Seconds and about 500.8 mPascal Seconds.

5. The lubricant base stock composition of claim 1, wherein the composition is void of carbon-carbon multiple bonds for enhanced oxidative stability.

6. The lubricant base stock composition of claim 1, wherein the composition thermal stability between about 300° C. through about 390° C.

7. The lubricant base stock composition of claim 1, wherein the composition has a crystallization onset of between about 37° C. down to about −90° C.

8. A lubricant composition comprising the lubricant base stock of claim 1 and one or more additives selected from the group consisting of detergents, antiwear agents, antioxidants, metal deactivators, extreme pressure (EP) additives, dispersants, viscosity index improvers, pour point depressants, corrosion protectors, friction coefficient modifiers, colorants, antifoam agents, and demulsifiers.

9. The lubricant composition of claim 8, wherein the lubricant composition is used in an application selected from the group consisting of two-cycle engine oils, hydraulic fluids, drilling fluids, greases, compressor oils, cutting fluids, milling fluids, and emulsifiers for metalworking fluids.

10. A lubricant composition comprising: (i) a lubricant base stock composition comprising a complex ester having the formula (I):

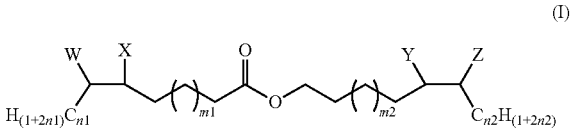

(I)

wherein n1=between 0 and 8; wherein n2=between 0 and 8; wherein m1=between 5 and 9; wherein m2=between 5 and 9; wherein W=OH or OCOR; wherein X=OH or OCOR; wherein Y=OCOR or OH; wherein Z=OH or OCOR; and in groups W, X, Y, and Z, R=CiHj, wherein i is 2 or greater and j is 5 or greater, and wherein the lubricant base stock composition has one or more of the following characteristics: (a) a melt onset of between about −5° C. down to about −90° C.; (b) a dynamic viscosity at 100° C. of between about 7.9 mPascal Seconds and about 33.5 mPascal Seconds; (c) a dynamic viscosity at 40° C. of between about 43.4 mPascal Seconds and about 500.8 mPascal Seconds; (d) a thermal stability between about 300° C. through about 390° C.; (e) a crystallization onset of between about 37° C. down to about −90° C.; and (f) is void of carbon -carbon multiple bonds for enhanced oxidative stability; and (ii) and one or more additives selected from the group consisting of detergents, antiwear agents, antioxidants, metal deactivators, extreme pressure (EP) additives, dispersants, viscosity index improvers, pour point depressants, corrosion protectors, friction coefficient modifiers, colorants, antifoam agents, and demulsifiers.

11. A lubricant composition comprising: (i) a lubricant base stock composition comprising a complex ester having the formula (I):

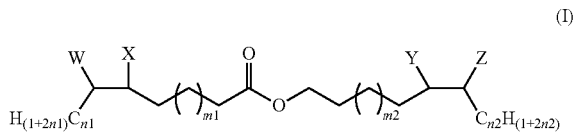

wherein n1=between 0 and 8; wherein n2=between 0 and 8; wherein m1=between 5 and 9; wherein m2=between 5 and 9; wherein W=OH or OCOR; wherein X=OH or OCOR; wherein Y=OCOR or OH; wherein Z=OH or OCOR; and in groups W, X, Y, and Z, R=CiHj, wherein i is 2 or greater and j is 5 or greater, and wherein the lubricant base stock composition has one or more of the following characteristics: (a) a melt onset of between about −5° C. down to about −90° C.; (b) a dynamic viscosity at 100° C. of between about 7.9 mPascal Seconds and about 33.5 mPascal Seconds; (c) a dynamic viscosity at 40° C. of between about 43.4 mPascal Seconds and about 500.8 mPascal Seconds; (d) a thermal stability between about 300° C. through about 390° C.; (e) a crystallization onset of between about 37° C. down to about −90° C.; and (f) is void of carbon-carbon multiple bonds for enhanced oxidative stability; and (ii) and one or more additives selected from the group consisting of detergents, antiwear agents, antioxidants, metal deactivators, extreme pressure (EP) additives, dispersants, viscosity index improvers, pour point depressants, corrosion protectors, friction coefficient modifiers, colorants, antifoam agents, and demulsifiers; and wherein the lubricant composition is used in an application selected from the group consisting of two-cycle engine oils, hydraulic fluids, drilling fluids, greases, compressor oils, cutting fluids, milling fluids, and emulsifiers for metalworking fluids.

12. The lubricant base stock composition of claim 1, wherein W, X, Y, and Z are each OCOR.

* * * * *